United States Patent
Maile et al.

(10) Patent No.: US 10,881,869 B2
(45) Date of Patent: Jan. 5, 2021

(54) WIRELESS RE-CHARGE OF AN IMPLANTABLE MEDICAL DEVICE

(71) Applicant: CARDIAC PACEMAKERS, INC., St. Paul, MN (US)

(72) Inventors: Keith R. Maile, New Brighton, MN (US); William J. Linder, Golden Valley, MN (US); Michael J. Kane, St. Paul, MN (US); Jeffrey E. Stahmann, Ramsey, MN (US); Jacob M. Ludwig, Isanti, MN (US); Brendan Early Koop, Ham Lake, MN (US); Daniel Joseph Landherr, Wyoming, MN (US); Greg Paul Carpenter, Centerville, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 476 days.

(21) Appl. No.: 15/812,783

(22) Filed: Nov. 14, 2017

(65) Prior Publication Data

US 2018/0140851 A1    May 24, 2018

Related U.S. Application Data

(60) Provisional application No. 62/424,918, filed on Nov. 21, 2016.

(51) Int. Cl.
  *A61N 1/378* (2006.01)
  *H02J 7/02* (2016.01)
  (Continued)

(52) U.S. Cl.
  CPC .......... *A61N 1/3787* (2013.01); *A61B 5/0031* (2013.01); *A61B 5/021* (2013.01);
  (Continued)

(58) Field of Classification Search
  CPC .............................. A61N 1/3787; H02J 50/80
  (Continued)

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2009231721 B2 | 10/2009 |
| AU | 2008279789 B2 | 10/2011 |

(Continued)

OTHER PUBLICATIONS

US 8,886,318 B2, 11/2014, Jacobson et al. (withdrawn)

(Continued)

*Primary Examiner* — Nadia A Mahmood
(74) *Attorney, Agent, or Firm* — Seager, Tufte & Wickhem LLP.

(57) ABSTRACT

Near-field energy transmitters for charging a rechargeable power source of an implantable medical device (IMD). In some cases, the transmitter may include an output driver that may drive a transmit coil such that near-field energy is transmitted to the IMD at a determined frequency. In some cases, the IMD may include a receiving coil that may capture the near-field energy and then convert the near-field energy into electrical energy that may be used to recharge the rechargeable power source. Since the rechargeable power source does not have to maintain sufficient energy stores in a single charge for the entire expected life of the IMD, the power source itself and thus the IMD may be made smaller while still meeting device longevity requirements.

19 Claims, 19 Drawing Sheets

(51) Int. Cl.

| | |
|---|---|
| *H02J 50/80* | (2016.01) |
| *A61N 1/375* | (2006.01) |
| *A61N 1/05* | (2006.01) |
| *A61B 5/0245* | (2006.01) |
| *A61N 1/365* | (2006.01) |
| *A61B 5/11* | (2006.01) |
| *A61B 5/021* | (2006.01) |
| *A61B 5/053* | (2006.01) |
| *H02J 50/12* | (2016.01) |
| *A61B 5/00* | (2006.01) |
| *H02J 7/00* | (2006.01) |
| *A61N 1/39* | (2006.01) |
| *H05K 5/00* | (2006.01) |
| *H01F 38/14* | (2006.01) |
| *H02J 50/70* | (2016.01) |
| *H01F 27/36* | (2006.01) |

(52) U.S. Cl.
CPC .......... *A61B 5/0245* (2013.01); *A61B 5/0538* (2013.01); *A61B 5/1116* (2013.01); *A61N 1/057* (2013.01); *A61N 1/365* (2013.01); *A61N 1/3756* (2013.01); *H02J 7/0042* (2013.01); *H02J 7/025* (2013.01); *H02J 50/12* (2016.02); *H02J 50/80* (2016.02); *A61B 2560/0219* (2013.01); *A61N 1/37512* (2017.08); *A61N 1/3956* (2013.01); *H01F 27/36* (2013.01); *H01F 38/14* (2013.01); *H02J 50/70* (2016.02); *H05K 5/0086* (2013.01); *H05K 5/0091* (2013.01)

(58) Field of Classification Search
USPC ............................................................ 607/2
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |

(56) References Cited

U.S. PATENT DOCUMENTS

| | | |
|---|---|---|
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,871,625 A | 2/1999 | Leddy et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,928,804 A | 7/1999 | Leddy et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,981,095 A | 11/1999 | Leddy et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A * | 9/2000 | Ryan .............. A61N 1/37223 128/903 |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,207,313 B1 | 3/2001 | Leddy et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,322,676 B1 | 11/2001 | Leddy et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,355,166 B1 | 3/2002 | Amarasinghe et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,479,176 B2 | 11/2002 | Leddy et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,766,200 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,890,670 B2 | 5/2005 | Leddy et al. |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |

(56) References Cited

U.S. PATENT DOCUMENTS

| | | |
|---|---|---|
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,225,032 B2 | 5/2007 | Schmeling et al. |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |

(56) References Cited

U.S. PATENT DOCUMENTS

| | | |
|---|---|---|
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Dulles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,140,168 B2 | 3/2012 | Olson et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,322 B2 | 10/2013 | Olson et al. |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,630,717 B2 | 1/2014 | Olson et al. |
| 8,634,908 B2 | 1/2014 | Cowan |

(56) References Cited

U.S. PATENT DOCUMENTS

| | | |
|---|---|---|
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,297 B2 | 12/2015 | Kast et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,333,365 B2 | 5/2016 | Zhao |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,405 B2 | 7/2016 | Hastings et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,431,694 B2 | 8/2016 | Li et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |

(56) References Cited

U.S. PATENT DOCUMENTS

| | | |
|---|---|---|
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0071328 A1 | 3/2008 | Haubrich et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0262573 A1 | 10/2008 | Seeberger et al. |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |

(56) References Cited

U.S. PATENT DOCUMENTS

| | | |
|---|---|---|
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0066211 A1 | 3/2011 | Von Arx et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |

(56) References Cited

U.S. PATENT DOCUMENTS

| | | |
|---|---|---|
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0224323 A1 | 8/2015 | Chen et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0059022 A1 | 3/2016 | Stahmann et al. |
| 2016/0101291 A1 | 4/2016 | Jaax et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |

FOREIGN PATENT DOCUMENTS

| | | |
|---|---|---|
| AU | 2008329620 B2 | 5/2014 |
| AU | 2014203793 A1 | 7/2014 |
| CA | 1003904 A1 | 1/1977 |
| CA | 2679413 C | 9/2008 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| EP | 2398556 B1 | 8/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 8500202 A1 | 1/1985 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |

(56) References Cited

FOREIGN PATENT DOCUMENTS

| | | |
|---|---|---|
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2017044904 A1 | 3/2017 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jan. 29, 2016, 15 pages.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

* cited by examiner

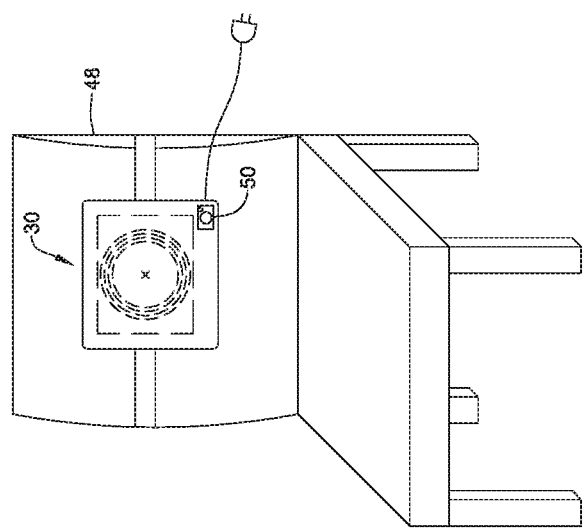

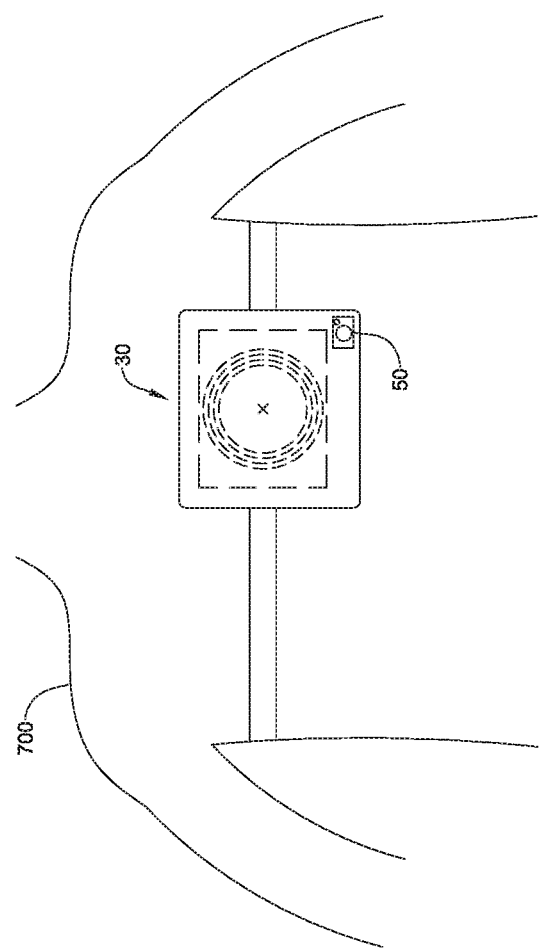

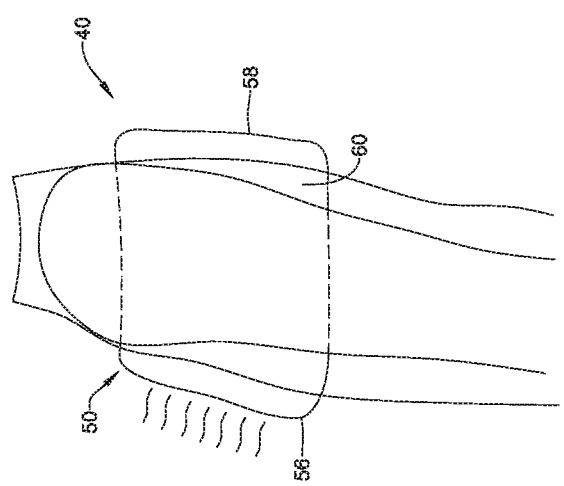

WIRELESS RE-CHARGE OF AN IMPLANTABLE MEDICAL DEVICE

CROSS REFERENCE TO RELATED APPLICATIONS

This application claims the benefit of U.S. Provisional Patent Application Ser. No. 62/424,918 filed on Nov. 21, 2016, the disclosure of which is incorporated herein by reference.

TECHNICAL FIELD

The disclosure relates generally to implantable medical devices, and more particularly to implantable medical devices that have a power source that may be wirelessly recharged from a remote location such as from outside of the body.

BACKGROUND

Implantable medical devices are commonly used to perform a variety of functions, such as to monitor one or more conditions and/or delivery therapy to a patient. In some cases, an implantable medical device may deliver neuro-stimulation therapy to a patient. In some cases, an implantable medical device may simply monitor one or more conditions, such as pressure, acceleration, cardiac events, and may communicate the detected conditions or events to another device, such as another implantable medical device or an external programmer.

In some cases, an implantable medical device may be configured to deliver pacing and/or defibrillation therapy to a patient. Such implantable medical devices may treat patients suffering from various heart conditions that may result in a reduced ability of the heart to deliver sufficient amounts of blood to a patient's body. In some cases, heart conditions may lead to rapid, irregular, and/or inefficient heart contractions. To help alleviate some of these conditions, various devices (e.g., pacemakers, defibrillators, etc.) may be implanted into a patient's body. When so provided, such devices can monitor and provide therapy, such as electrical stimulation therapy, to the patient's heart to help the heart operate in a more normal, efficient and/or safe manner. In some cases, a patient may have multiple implanted devices that cooperate to monitor and/or provide therapy to the patient's heart.

Some implantable medical devices must be relatively small because of anatomical constraints. For example, leadless cardiac pacemakers are often placed within a heart chamber. Due to their relatively small size, and because of their long life expectancy, a large fraction of the internal space of such implantable medical devices is often consumed by a battery or other power source. As the battery life determines the useful life expectancy of the implantable medical device, there is a desire to make the batteries as large as possible within the confines of the available space.

What would be desirable is an implantable medical device that has recharge capability for recharging a rechargeable power source of the implantable medical device. This may give the implantable medical device a longer useful life expectancy and/or may not require as much battery space permitting a significantly smaller device size. A smaller device size may make the device more easily deliverable and implantable in the body, allow the device to be implantable in smaller and more confined spaces in the body, and/or may make the device less expensive to produce.

SUMMARY

The disclosure is directed to charging/recharging a power source of an implantable medical devices. While a leadless cardiac pacemaker is used as an example implantable medical device, it should be understood that the disclosure can be applied to any suitable implantable medical device including, for example, neuro-stimulators, diagnostic devices including those that do not deliver therapy, and/or any other suitable implantable medical device as desired.

In some cases, the disclosure pertains to a near-field energy transmitter for charging an implantable medical devices (IMD) such as leadless cardiac pacemakers (LCP) that include a rechargeable power source such as a rechargeable battery, a rechargeable capacitor or a rechargeable supercapacitor. In some cases, the transmitter may include an output drive that may drive a transmit coil such that the near-field energy is transmitted to the IMD at a determined frequency and amplitude. In some cases, the IMD may include a receiving coil that may capture the near-field energy and then convert the near-field energy into electrical energy that may be used to recharge the rechargeable power source. Accordingly, since the rechargeable power source does not have to maintain sufficient energy stores in a single charge for the entire expected lifetime of the IMD, the power source itself and thus the IMD may be made smaller while still meeting device longevity requirements.

In an example of the disclosure, a near-field energy transmitter for charging an IMD may include a transmit coil configured to transmit near-field energy to the IMD. An output driver may be configured for driving the transmit coil so that the transmit coil may transmit the near-field energy at a transmit frequency, wherein the transmit frequency may be adjustable. A monitor may be operatively coupled to the output driver and may detect a transmit power of the transmitted near-field energy. A controller may be operatively coupled to the output driver and the monitor and the controller may be configured to cause the output driver to adjust the transmit frequency of the near-field energy across two or more transmit frequencies, identify the transmit power of the near-field energy at each of the two or more transmit frequencies using the monitor, select the transmit frequency of the two or more transmit frequencies that results in a transmit power that has a predetermined characteristic, and set the transmit frequency of the output driver to the selected transmit frequency.

Alternatively or additionally to any of the embodiments above, the predetermined characteristic of the transmit power may be that the transmit power is the maximum transmit power identified for the two or more transmit frequencies.

Alternatively or additionally to any of the embodiments above, at least one of the transmit frequencies is a resonant frequency of the output driver and transmit coil, and the output driver includes an adjustable impedance that is adjustable to produce the resonance frequency.

Alternatively or additionally to any of the embodiments above, the controller may be configured to detect a decrease in the transmit power at the selected transmit frequency, and in response may cause the output driver to adjust the transmit frequency of the near-field energy across two or more transmit frequencies, identify the transmit power of the near-field energy at each of the two or more transmit frequencies, select the transmit frequency of the two or more transmit frequencies that results in a transmit power that has a predetermined characteristic, and set the transmit frequency of the output driver to the selected transmit frequency.

Alternatively or additionally to any of the embodiments above, the controller may be configured to repeat from time to time the following: cause the output driver to adjust the transmit frequency of the near-field energy across two or more transmit frequencies, identify the transmit power of the near-field energy at each of the two or more transmit frequencies, select the transmit frequency of the two or more transmit frequencies that results in a transmit power that has a predetermined characteristic, and set the transmit frequency of the output driver to the selected transmit frequency.

Alternatively or additionally to any of the embodiments above, the near-field energy transmitter may further include a posture sensor for detecting a posture of a patient in which the implantable medical device is implanted, and wherein the controller may be configured to identify a transmit frequency for each of two or more postures by using the posture sensor to detect when the patient is in one of the two or more postures, and when in the detected posture, cause the output driver to adjust the transmit frequency of the near-field energy across two or more transmit frequencies, identify the transmit power of the near-field energy at each of the two or more transmit frequencies using the monitor, select the transmit frequency of the two or more transmit frequencies that results in a transmit power that has a predetermined characteristic, and associate the detected posture with the selected transmit frequency.

Alternatively or additionally to any of the embodiments above, the controller may be further configured to subsequently detect when the patient is in one of the two or more postures, and in response, set the transmit frequency of the output driver to the transmit frequency that is associated with the detected posture.

Alternatively or additionally to any of the embodiments above, the near-field energy transmitter may further include a communication block for communicating with the implantable medical device, and wherein the communication block may be configured to receive one or more messages from the implantable medical device regarding the transmit power that is received by the implantable medical device.

Alternatively or additionally to any of the embodiments above, the output driver may be configured to drive the transmit coil so that the transmit coil transmits the near-field energy at a transmit amplitude, wherein the transmit amplitude may be adjustable, and the controller may be configured to adjust the transmit amplitude of the near-field energy so that the transmit power that is received by the implantable medical device meets a predetermined characteristic, condition or criteria.

Alternatively or additionally to any of the embodiments above, the transmit coil may comprise a plurality of transmit coils and the output driver may be configured to drive the plurality of transmit coils so that the plurality of transmit coils may transmit the near-field energy along a transmit vector, wherein the transmit vector may be adjustable, and the controller may be configured to adjust the transmit vector of the near-field energy so that the transmit power that is received by the IMD may meet a predetermined criteria.

Alternatively or additionally to any of the embodiments above, the one or more messages received from the implantable medical device may indicate whether the transmit power that is received by the implantable medical device meets the predetermined characteristic, condition or criteria.

Alternatively or additionally to any of the embodiments above, the one or more messages received from the implantable medical device may indicate whether the transmit power that is received by the implantable medical device does not meet the predetermined characteristic, condition or criteria.

Alternatively or additionally to any of the embodiments above, the near-field energy transmitter may further include a flexible substrate configured to conform to a patient and house the transmitter coil.

Alternatively or additionally to any of the embodiments above, the flexible substrate may include a strap for securing the flexible substrate in place, and wherein the flexible substrate may have target fiducials to indicate a torso position of the patient relative to the transmit coil.

Alternatively or additionally to any of the embodiments above, the near-field energy transmitter may further include a ferromagnetic shield along a side of the transmit coil that may face away from the implantable medical device during use.

Alternatively or additionally to any of the embodiments above, the flexible substrate may be configured to be worn by the patient.

Alternatively or additionally to any of the embodiments above, the near-field energy transmitter may further include a second transmit coil housed by the flexible substrate, wherein the transmit coil may be configured to be located on a front of the patient and the second transmit coil may be configured to be located on a side or back of the patient.

Alternatively or additionally to any of the embodiments above, the controller may be further configured to issue a human perceptible alert if the transmit coil is deemed to be misaligned with the implantable medical device.

In another example of the disclosure, a near-field energy transmitter for charging an implantable medical device (IMD) may include a transmit coil that may be configured to transmit near-field energy to the implantable medical device. An output driver for driving the transmit coil may be provided. The output driver may cause the transmit coil to transmit the near-field energy at a transmit frequency and a transmit amplitude, wherein at least one of the transmit frequency and transmit amplitude may be adjustable. A communication block may be included for communicating with the implantable medical device. The communication block may be configured to receive one or more messages from the implantable medical device regarding the transmit power that is received by the implantable medical device. A controller may be operatively coupled to the output driver and the communication block. The controller may be configured to adjust one or more of the transmit frequency and transmit amplitude of the near-field energy so that the transmit power that is received by the implantable medical device may meet a predetermined characteristic, condition or criteria.

Alternatively or additionally to any of the embodiments above, the one or more messages received from the implantable medical device may indicate whether the transmit power that is received by the implantable medical device meets the predetermined characteristic, condition or criteria, and/or whether the transmit power that is received by the implantable medical device does and/or does not meet the predetermined characteristic, condition or criteria.

In another example of the disclosure, a near-field energy transmitter for chagrining an implantable medical device (IMD) may include one or more transmit coils that may be configured to transmit near-field energy to the IMD. An output driver that may drive the one or more transmit coils so that the one or more transmit coils may transmit the near-field energy at a transmit frequency, a transmit vector and a transmit amplitude, wherein at least one of the transmit frequency, transmit vector and transmit amplitude is adjustable, a communication block that may communicate with the IMD, wherein the communication block may be configured to receive one or more messages from the IMD regarding the transmit power that is received by the IMD, and a controller that may be operatively coupled to the output driver and the communication block, the controller may be configured to adjust one or more of the transmit frequency, the transmit vector and the transmit amplitude of the near-field energy so that the transmit power that is received by the IMD may meet a predetermined criteria.

In another example of the disclosure, an implantable medical device (IMD) may be configured to be implanted within a patient's body and may include a housing that may be configured for trans-catheter deployment. A plurality of electrodes that may be exposed external to the housing. Therapeutic circuitry that may be disposed within the housing and may be operatively coupled to the plurality of electrodes and may be configured to sense one or more signals via one or more of the plurality of electrodes and/or to stimulate tissue via one or more of the plurality of electrodes. A rechargeable power source may be disposed within the housing and may be configured to power the therapeutic circuitry. A receiving coil may be configured to receive non-radiative near-field energy through the patient's body. Charging circuitry may be operatively coupled with the receiving coil and the rechargeable power source and may be configured to use the non-radiative near-field energy received via the receiving coil to charge the rechargeable power source. A controller may be disposed within the housing and may be configured to detect whether the non-radiative near-field energy received by the receiving coil meets a predetermined characteristic, condition or criteria and communicate a message to a remotely located near-field energy transmitter indicating if the non-radiative near-field energy received by the receiving coil meets and/or does not meet the predetermined characteristic, condition or criteria.

BRIEF DESCRIPTION OF THE FIGURES

The disclosure may be more completely understood in consideration of the following description in connection with the accompanying drawings, in which:

FIG. 14B is an illustrative flexible substrate, placed on a chair, that may house a transmit coil according to an example of the disclosure;

FIG. 14C is an illustrative flexible substrate, worn by a patient, that may house a transmit coil according to an example of the disclosure;

FIG. 15B is an illustrative flexible substrate, worn by a patient, that may house two transmit coils according to an example of the disclosure.

Figure 1:
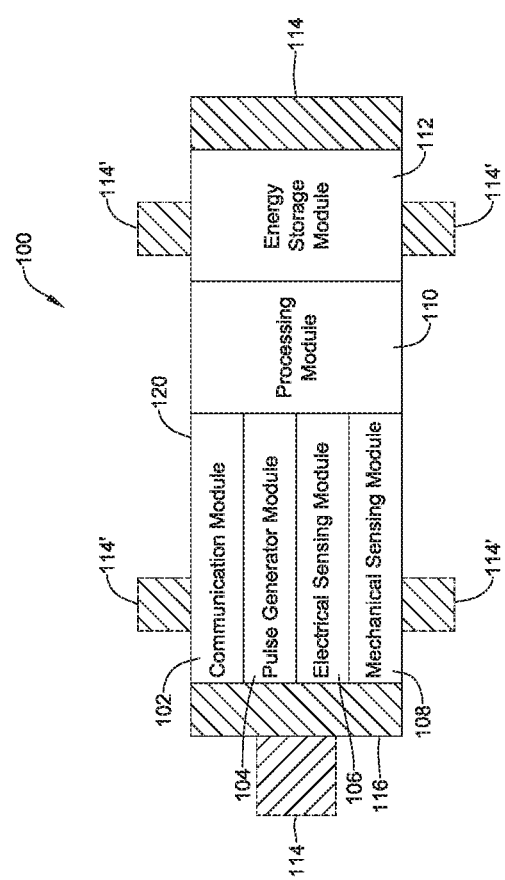
FIG. 1 is a schematic block diagram of an illustrative LCP in accordance with an example of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure. While a leadless cardiac pacemaker is used as an example implantable medical device, it should be understood that the disclosure can be applied to any suitable implantable medical device including, for example, neuro-stimulators, diagnostic devices including those that do not deliver therapy, and/or any other suitable implantable medical device as desired.

FIG. 1 depicts an illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 1, the LCP 100 may be a compact device with all components housed within the or directly on a housing 120. In some cases, the LCP 100 may be considered as being an example of an implantable medical device (IMD). In the example shown in FIG. 1, the LCP 100 may include a communication module 102, a pulse generator module 104, an electrical sensing module 106, a mechanical sensing module 108, a processing module 110, a battery 112, and an electrode arrangement 114. The LCP 100 may include more or less modules, depending on the application.

The communication module 102 may be configured to communicate with devices such as sensors, other medical devices such as an SICD, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device (e.g. SICD and/or programmer) through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

In the example shown in FIG. 1, the pulse generator module 104 may be electrically connected to the electrodes 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate and deliver electrical stimulation signals by using energy stored in the battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate and deliver electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy. In some cases, the pulse generator 104 may provide a controllable pulse energy. In some cases, the pulse generator 104 may allow the controller to control the pulse voltage, pulse width, pulse shape or morphology, and/or any other suitable pulse characteristic.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' may represent ventricular cardiac electrical signals. In some cases, the LCP 100 may be configured to detect cardiac electrical signals from other chambers (e.g. far field), such as the P-wave from the atrium.

The mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 1 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulative portion that electrically isolates the electrodes 114/114' from adjacent electrodes, the housing 120, and/or other parts of the LCP 100. In some cases, one or more of the electrodes 114/114' may be provided on a tail (not shown) that extends away from the housing 120.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, abnormalities in the operation of the heart H. Based on any determined abnormalities, the processing module 110 may control the pulse generator module 104 to generate and deliver electrical stimulation in accordance with one or more therapies to treat the determined abnormalities. The processing module 110 may further receive information from the communication module 102. In some examples, the processing module 110 may use such received information to help determine whether an abnormality is occurring, determine a type of abnormality, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In other examples, the battery 112 may be some other type of power source, as desired. In some cases, the battery 112 may not be battery at all, but rather may be super capacitor or other charge storage device. In some cases, the LCP 100 may include a receiver coil for receiving near-field energy. Charging circuitry may be operatively coupled with the receiving coil and the battery 112, and may be configured to use the non-radiative near-field energy received via the receiving coil to charge the battery 112.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
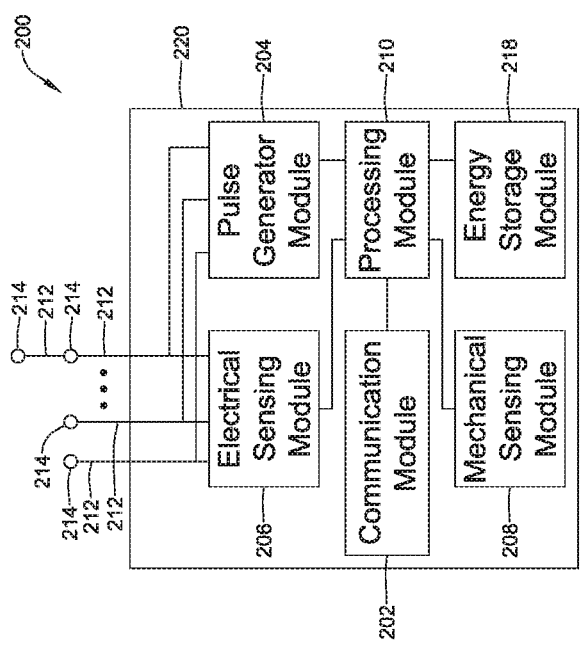
FIG. 2 is a schematic block diagram of another illustrative medical device that may be used in conjunction with the LCP of FIG. 1.

FIG. 2 depicts an example of another or second medical device (MD) 200, which may be used in conjunction with the LCP 100 (FIG. 1) in order to detect and/or treat cardiac abnormalities. In some cases, the MD 200 may be considered as an example of the IMD and/or the LCP. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of LCP 100. Additionally, the battery 218 may be similar to the battery 112 of the LCP 100. In some examples, however, the MD 200 may have a larger volume within the housing 220. In such examples, the MD 200 may include a larger battery and/or a larger processing module 210 capable of handling more complex operations than the processing module 110 of the LCP 100.

While it is contemplated that the MD 200 may be another leadless device such as shown in FIG. 1, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, acoustic sensors, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some instances, the lead(s) may have one or more electrodes that are placed subcutaneously and outside of the chest cavity. In other examples, the lead(s) may have one or more electrodes that are placed inside of the chest cavity, such as just interior of the sternum but outside of the heart H.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy.

In some cases, the MD 200 may be external to the patient's body and may include a transmit coil that is configured to transmit near-field energy to an implanted IMD. The MD 200 may also include an output driver for driving the transmit coil at a transmit frequency and a transmit amplitude. The transmit frequency and/or transmit amplitude may be tuned, sometimes actively tuned, so as to deliver an acceptable transmit power to a receive coil of the implanted IMD. The transmit power may be used to recharge a power source of the implanted IMD.

Figure 3:
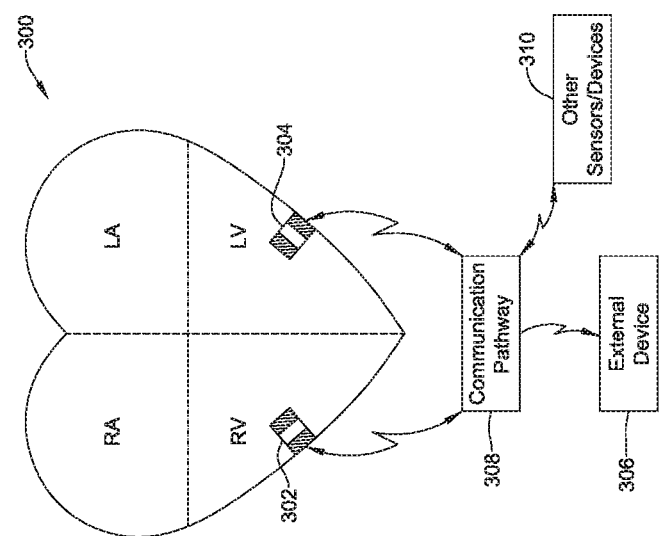
FIG. 3 is a schematic diagram of an exemplary medical system that includes multiple LCPs and/or other devices in communication with one another.

FIG. 3 illustrates an example of a medical device system and a communication pathway through which multiple medical devices 302, 304, 306, and/or 310 may communicate. In the example shown, the medical device system 300 may include LCPs 302 and 304, external medical device 306, and other sensors/devices 310. The external device 306 may be any of the devices described previously with respect to the MD 200. Other sensors/devices 310 may also be any of the devices described previously with respect to the MD 200. In some instances, other sensors/devices 310 may include a sensor, such as an accelerometer, an acoustic sensor, a blood pressure sensor, or the like. In some cases, other sensors/devices 310 may include an external programmer device that may be used to program one or more devices of the system 300.

Various devices of the system 300 may communicate via communication pathway 308. For example, the LCPs 302 and/or 304 may sense intrinsic cardiac electrical signals and may communicate such signals to one or more other devices 302/304, 306, and 310 of the system 300 via communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. It is contemplated that the communication pathway 308 may communicate using RF signals, inductive coupling, optical signals, acoustic signals, or any other signals suitable for communication. Additionally, in at least some examples, communication pathway 308 may include multiple signal types. For instance, other sensors/device 310 may communicate with the external device 306 using a first signal type (e.g. RF communication) but communicate with the LCPs 302/304 using a second signal type (e.g. conducted communication). Further, in some examples, communication between devices may be limited. For instance, as described above, in some examples, the LCPs 302/304 may communicate with the external device 306 only through other sensors/devices 310, where the LCPs 302/304 send signals to other sensors/devices 310, and other sensors/devices 310 relay the received signals to the external device 306.

In some cases, the communication pathway 308 may include conducted communication. Accordingly, devices of the system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-capture threshold to the heart. Although, in some cases, the amplitude/pulse width of the delivered electrical communication pulses may be above the capture threshold of the heart, but may be delivered during a blanking period of the heart (e.g. refractory period) and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired. Alternatively, or in addition, the communication pathway 308 may include radiofrequency (RF) communication, inductive communication, optical communication, acoustic communication and/or any other suitable communication, as desired.

Figure 4:
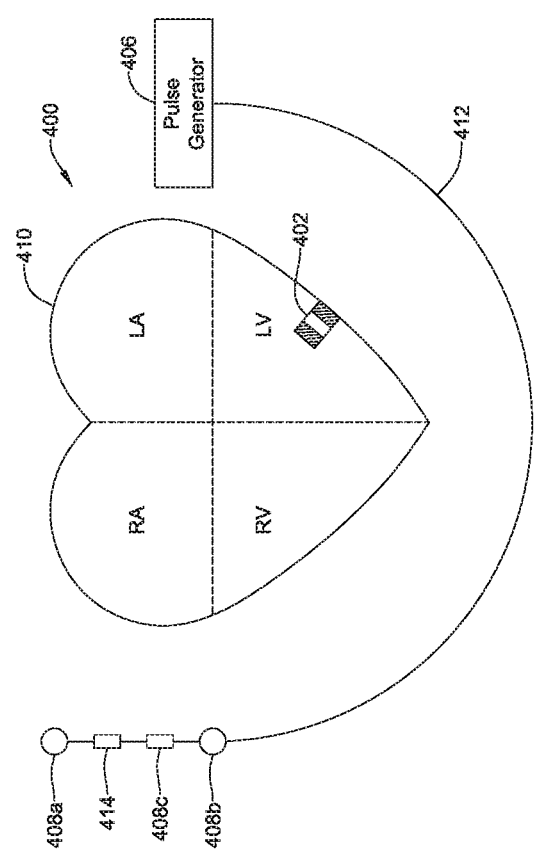
FIG. 4 is a schematic diagram of a system including an LCP and another medical device, in accordance with an example of the disclosure.

FIG. 4 shows an illustrative medical device system. In FIG. 4, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously. In some cases, the one or more electrodes 408a-408c may be placed inside of the chest cavity but outside of the heart, such as just interior of the sternum.

In some cases, the LCP 402 may communicate with the subcutaneous implantable cardioverter-defibrillator (S-ICD). In some cases, the lead 412 and/or pulse generator 406 may include an accelerometer 414 that may, for example, be configured to sense vibrations that may be indicative of heart sounds.

In some cases, the LCP 402 may be in the right ventricle, right atrium, left ventricle or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

Figure 5:
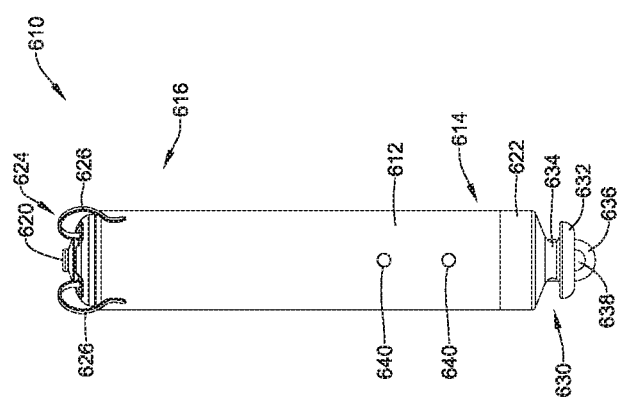
FIG. 5 is a side view of an illustrative implantable leadless cardiac device.

FIG. 5 is a side view of an illustrative implantable leadless cardiac pacemaker (LCP) 610. The LCP 610 may be similar in form and function to the LCP 100 described above. The LCP 610 may include any of the modules and/or structural features described above with respect to the LCP 100 described above. The LCP 610 may include a shell or housing 612 having a proximal end 614 and a distal end 616. The illustrative LCP 610 includes a first electrode 620 secured relative to the housing 612 and positioned adjacent to the distal end 616 of the housing 612 and a second electrode 622 secured relative to the housing 612 and positioned adjacent to the proximal end 614 of the housing 612. In some cases, the housing 612 may include a conductive material and may be insulated along a portion of its length. A section along the proximal end 614 may be free of insulation so as to define the second electrode 622. The electrodes 620, 622 may be sensing and/or pacing electrodes to provide electro-therapy and/or sensing capabilities. The first electrode 620 may be capable of being positioned against or may otherwise contact the cardiac tissue of the heart while the second electrode 622 may be spaced away from the first electrode 620. The first and/or second electrodes 620, 622 may be exposed to the environment outside the housing 612 (e.g. to blood and/or tissue).

In some cases, the LCP 610 may include a pulse generator (e.g., electrical circuitry) and a power source (e.g., a battery) within the housing 612 to provide electrical signals to the electrodes 620, 622 to control the pacing/sensing electrodes 620, 622. While not explicitly shown, the LCP 610 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing 612. Electrical connections between the pulse generator and the electrodes 620, 622 may allow electrical stimulation to heart tissue and/or sense a physiological condition.

In the example shown, the LCP 610 includes a fixation mechanism 624 proximate the distal end 616 of the housing 612. The fixation mechanism 624 is configured to attach the LCP 610 to a wall of the heart H, or otherwise anchor the LCP 610 to the anatomy of the patient. In some instances, the fixation mechanism 624 may include one or more, or a plurality of hooks or tines 626 anchored into the cardiac tissue of the heart H to attach the LCP 610 to a tissue wall. In other instances, the fixation mechanism 624 may include one or more, or a plurality of passive tines, configured to entangle with trabeculae within the chamber of the heart H and/or a helical fixation anchor configured to be screwed into a tissue wall to anchor the LCP 610 to the heart H. These are just examples.

The LCP 610 may further include a docking member 630 proximate the proximal end 614 of the housing 612. The docking member 630 may be configured to facilitate delivery and/or retrieval of the LCP 610. For example, the docking member 630 may extend from the proximal end 614 of the housing 612 along a longitudinal axis of the housing 612. The docking member 630 may include a head portion 632 and a neck portion 634 extending between the housing 612 and the head portion 632. The head portion 632 may be an enlarged portion relative to the neck portion 634. For example, the head portion 632 may have a radial dimension from the longitudinal axis of the LCP 610 that is greater than a radial dimension of the neck portion 634 from the longitudinal axis of the LCP 610. In some cases, the docking member 630 may further include a tether retention structure 636 extending from or recessed within the head portion 632. The tether retention structure 636 may define an opening 638 configured to receive a tether or other anchoring mechanism therethrough. While the retention structure 636 is shown as having a generally "U-shaped" configuration, the retention structure 636 may take any shape that provides an enclosed perimeter surrounding the opening 638 such that a tether may be securably and releasably passed (e.g. looped) through the opening 638. In some cases, the retention structure 636 may extend though the head portion 632, along the neck portion 634, and to or into the proximal end 614 of the housing 612. The docking member 630 may be configured to facilitate delivery of the LCP 610 to the intracardiac site and/or retrieval of the LCP 610 from the intracardiac site. While this describes one example docking member 630, it is contemplated that the docking member 630, when provided, can have any suitable configuration.

It is contemplated that the LCP 610 may include one or more pressure sensors 640 coupled to or formed within the housing 612 such that the pressure sensor(s) is exposed to the environment outside the housing 612 to measure blood pressure within the heart. For example, if the LCP 610 is placed in the left ventricle, the pressure sensor(s) 640 may measure the pressure within the left ventricle. If the LCP 610 is placed in another portion of the heart (such as one of the atriums or the right ventricle), the pressures sensor(s) may measure the pressure within that portion of the heart. The pressure sensor(s) 640 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 640 may be part of a mechanical sensing module described herein. It is contemplated that the pressure measurements obtained from the pressures sensor(s) 640 may be used to generate a pressure curve over cardiac cycles. The pressure readings may be taken in combination with impedance measurements (e.g. the impedance between electrodes 620 and 622) to generate a pressure-impedance loop for one or more cardiac cycles as will be described in more detail below. The impedance may be a surrogate for chamber volume, and thus the pressure-impedance loop may be representative for a pressure-volume loop for the heart H.

In some embodiments, the LCP 610 may be configured to measure impedance between the electrodes 620, 622. More generally, the impedance may be measured between other electrode pairs, such as the additional electrodes 114' described above. In some cases, the impedance may be measure between two spaced LCP's, such as two LCP's implanted within the same chamber (e.g. LV) of the heart H, or two LCP's implanted in different chambers of the heart H (e.g. RV and LV). The processing module of the LCP 610 and/or external support devices may derive a measure of cardiac volume from intracardiac impedance measurements made between the electrodes 620, 622 (or other electrodes). Primarily due to the difference in the resistivity of blood and the resistivity of the cardiac tissue of the heart H, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy or the like, and the measured impedance may be correlated to the actual cardiac volume.

In some cases, the LCP 610 may be provided with energy delivery circuitry operatively coupled to the first electrode 620 and the second electrode 622 for causing a current to flow between the first electrode 620 and the second electrode 622 in order to determine the impedance between the two electrodes 620, 622 (or other electrode pair). It is contemplated that the energy delivery circuitry may also be configured to deliver pacing pulses via the first and/or second electrodes 620, 622. The LCP 610 may further include detection circuitry operatively coupled to the first electrode 620 and the second electrode 622 for detecting an electrical signal received between the first electrode 620 and the second electrode 622. In some instances, the detection circuitry may be configured to detect cardiac signals received between the first electrode 620 and the second electrode 622.

When the energy delivery circuitry delivers a current between the first electrode 620 and the second electrode 622, the detection circuitry may measure a resulting voltage between the first electrode 620 and the second electrode 622 (or between a third and fourth electrode separate from the first electrode 620 and the second electrode 622, not shown) to determine the impedance. When the energy delivery circuitry delivers a voltage between the first electrode 620 and the second electrode 622, the detection circuitry may measure a resulting current between the first electrode 620 and the second electrode 622 (or between a third and fourth electrode separate from the first electrode 620 and the second electrode 622) to determine the impedance.

Figure 6:
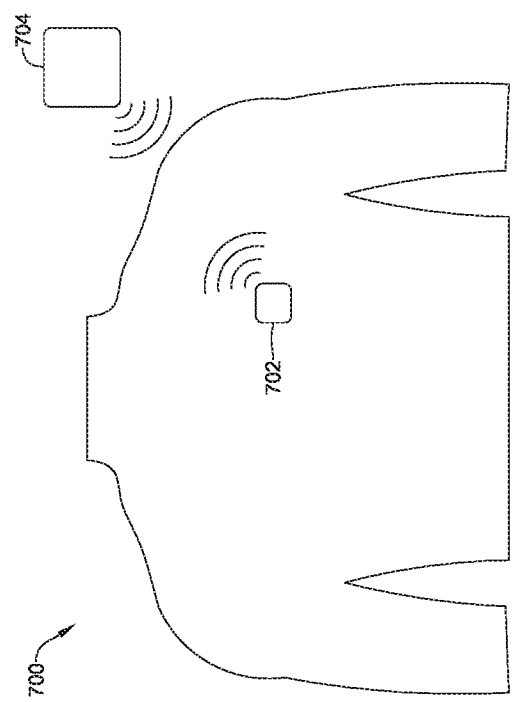
FIG. 6 is a schematic diagram of a patient with a rechargeable implantable medical device system.

FIG. 6 provides a highly schematic illustration of a patient 700 having an implantable device (IMD) 702 implanted within the patient 700. While the IMD 702 is shown as being in or near the patient's chest, it will be appreciated that this is merely illustrative, as the IMD 702, depending on functionality, may be implanted in other locations within the patient 700. A transmitter 704 is shown exterior to the patient 700. In some cases, the transmitter 704 may be configured to transmit reactive near-field energy that is of a wavelength (or frequency, as wavelength and frequency are related by the numerical speed of light) and amplitude that can safety pass into the patient 700 to the IMD 702 without causing excessive tissue heating or other potentially damaging effects to the patient 700.

The transmitter 704 may take any suitable form. For example, while shown schematically as a box in FIG. 6, the transmitter 704 may be sized and configured for the patient 700 to periodically wear about their neck on a lanyard or in a shirt pocket, which would place the transmitter 704 proximate their chest, at about the same vertical and horizontal position as the IMD 702 within the patient's chest. In some cases, the transmitter 704 may be built into the back of a chair that the patient 700 would periodically sit in to recharge the IMD 702. The chair could be in the patient's home, for a daily recharge, for example, or could be at a remote location such as a medical clinic, for a patient 700 having a longer recharge schedule.

As another example, the transmitter 704 could be built into a bed such that the transmitter 704 could at least partially recharge the IMD 702 each evening when the patient 700 sleeps. In some cases, the transmitter 704 could be configured to only transmit once per week, or once per month, for example, depending on the power requirements of the IMD 702. In some cases, the transmitter 704 and the IMD 702 may communicate with each other. When so provided, the IMD 702 may report its current battery recharge level to the transmitter 704, and if the current battery recharge level is below a threshold, the transmitter 704 may transmit power to the IMD 702.

It will be appreciated that the IMD 702 may be configured to periodically receive near-field energy at a wavelength and intensity that is safe for the patient 700 and that the IMD 702 may use to recharge a rechargeable power source within the IMD 702. The near-field energy may be received at a rate that exceeds a rate at which power is being drawn from the rechargeable battery and consumed by various components within the IMD 702.

Figure 7:
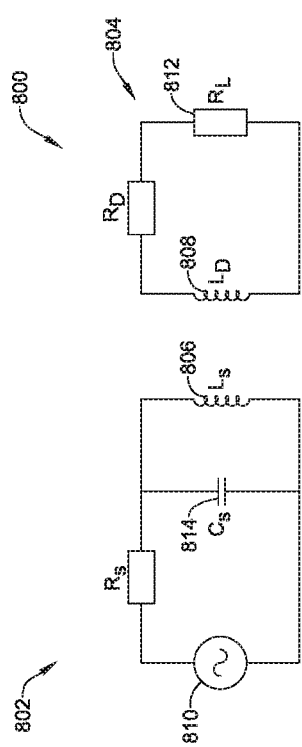
FIG. 7 is a schematic of an illustrative circuit for a coupled inductor system.

FIG. 7 provides an illustrative circuit for a coupled inductor system 800. Inductive coupling is the near-field wireless transmission of electrical energy between a source 802 and a device 804. In some cases, the source 802 may transfer power from a source inductor 806 (e.g. source coil) to a device inductor 808 (e.g. device coil) by a magnetic field. The system 800, therefore, may act as a transformer. In some cases, a signal generator 810 may generate an alternating current (AC) through the source inductor 806 and create an oscillating magnetic field. The signal generator 810 may include an output driver. The magnetic field may pass through the device inductor 808 and induce an alternating electromagnetic force (EMF), which creates an alternating current (AC) in the device 804. The induced AC may either drive a load 812 directly, or be rectified to direct current (DC) by a rectifier (not shown) in the device 804, which drives the load 812.

In some cases, the power transferred may increase with frequency and mutual inductance between the source inductor 806 and the device inductor 808, which may depend on their geometry and the distance between them. For example, if the source inductor 806 and the device inductor 808 are on the same axis (i.e., a primary capture axis) and close together so the magnetic flux from the source inductor 806 passes through the device inductor 808, the transfer of power may approach 100%. The greater the separation between the coils, the more the magnetic flux from the source inductor 806 may miss the device inductor 808, and the transfer of power may decrease.

In some cases, the source inductor 806 and/or the device inductor 808 may be fitted with magnetic cores. A magnetic core can be a piece of magnetically active material with a high magnetic permeability used to confine and guide magnetic fields in electrical, electromechanical and magnetic devices such as electromagnets, transformers, generators, inductors, and other magnetic assemblies. In some cases, the magnetic core may be made of ferromagnetic metal such as iron, or ferromagnetic compounds such as ferrites. The high permeability, relative to the surrounding atmosphere, may cause the magnetic field lines to be concentrated in the ferrite core. In some cases, the use of the ferrite core can concentrate the strength and increase the effect of magnetic fields produced by the source inductor 806 and may improve inductive coupling and the transfer of power.

In some cases, the system may achieve resonant inductive coupling. In this case, the source 802 can be tuned to resonant at the same frequency as the device 804. In some cases, the source 802 can include the source inductor 806 connected to a capacitor 814. The resonance between the source inductor 806 and the device inductor 808 can increase the coupling and the transmitted power. In some cases, when the system 800 achieves resonant inductive coupling, the source 802 and the device 804 may interact with each other more strongly than they do with non-resonant objects and power losses due to absorption in stray nearby objects may be reduced.

Figure 8:
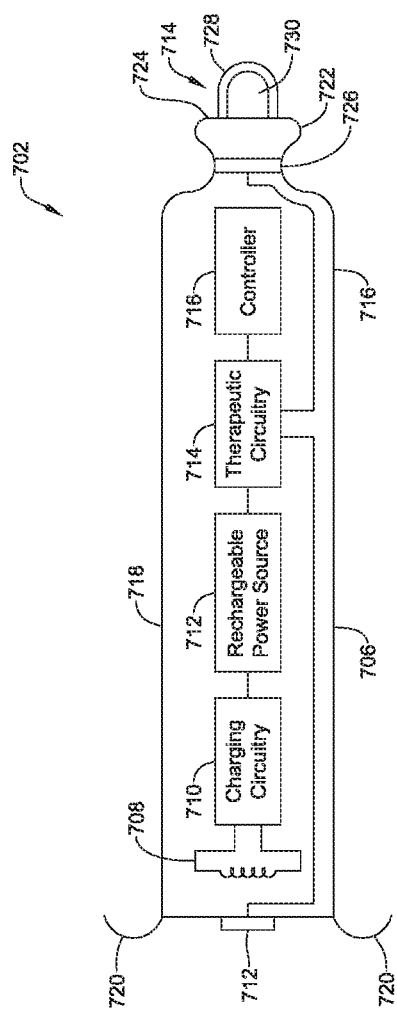
FIG. 8 is a schematic diagram of an illustrative implantable medical device (IMD) according to an example of the disclosure.

FIG. 8 provides a cross-sectional view of the illustrative IMD 702. In some cases, the IMD 702 includes a device housing 706 that may encompass a receiving coil 708, charging circuitry 710, a rechargeable power source 712, therapeutic circuitry 714, and a controller 717. In various embodiments, the housing 706 may have a proximal end 716 and a distal end 718. The IMD 702 may include a first electrode 715 positioned adjacent to the distal end 718 of the housing 706 and a second electrode 719 positioned adjacent to the proximal end 716 of the housing 706. In some cases, the housing 706 may include a conductive material and may be insulated along a portion of its length. A section along the proximal end 716 may be free of insulation so as to define the second electrode 719. This is just one example implementation. The electrodes 715, 719 may be sensing and/or pacing electrodes to provide electro-therapy and/or sensing capabilities. The first electrode 715 may be capable of being positioned against or may otherwise contact cardiac tissue of a heart while the second electrode 719 may be spaced away from the first electrode 715, and thus spaced away from the cardiac tissue.

The illustrative IMD 702 may include a fixation mechanism 720 proximate the distal end 718 of the housing 706, which may be configured to attach the IMD 702 to a tissue wall of the heart, or otherwise anchor the IMD 702 to the anatomy of the patient. As shown in FIG. 8, in some instances, the fixation mechanism 720 may include one or more, or a plurality of hooks or tines anchored into the cardiac tissue of the heart to attach the IMD 702 to the tissue wall. In other instances, the fixation mechanism 720 may include one or more, or a plurality of passive tines, configured to entangle with trabeculae within the chamber of the heart and/or a helical fixation anchor configured to be screwed into the tissue wall to anchor the IMD 702 to the heart.

In some cases, the IMD 702 may include a docking member 722 proximate the proximal end 716 of the housing 706 configured to facilitate delivery and/or retrieval of the IMD 702. For example, the docking member 722 may extend from the proximal end 716 of the housing 706 along a longitudinal axis of the housing 706. The docking member 722 may include a head portion 724 and a neck portion 726 extending between the housing 706 and the head portion 724. The head portion 724 may be an enlarged portion relative to the neck portion 726. For example, the head portion 724 may have a radial dimension from the longitudinal axis of the IMD 702 which is greater than a radial dimension of the neck portion 726 from the longitudinal axis of the IMD 702. The docking member 722 may further include a tether retention structure 728 extending from the head portion 724. The tether retention structure 728 may define an opening 730 configured to receive a tether or other anchoring mechanism therethrough. While the retention structure 728 is shown as having a generally "U-shaped" configuration, the retention structure 728 may take any shape which provides an enclosed perimeter surrounding the opening 730 such that a tether may be securably and releasably passed (e.g. looped) through the opening 730. The retention structure 728 may extend though the head portion 724, along the neck portion 726, and to or into the proximal end 716 of the housing 706. The docking member 722 may be configured to facilitate delivery of the IMD 702 to the intracardiac site and/or retrieval of the IMD 702 from the intracardiac site. Other docking members 722 are contemplated.

According to various embodiments, the housing may also be configured for trans-catheter deployment. In some cases, this means that the housing 706 has overall dimensions that enable the IMD 702 to fit within a catheter or similar device for delivering the IMD 702 via a vascular approach. In some cases, the housing 706 may have an overall length of perhaps about 50 millimeters or less, or perhaps about 30 millimeters or less, and/or an overall width of perhaps about 20 millimeters or less, or perhaps about 10 millimeters or less. These are just examples.

In some cases, the receiving coil 708 may be any of a variety of different types of coils. When considering the electromagnetic regions around a transmitting coil/antenna, there are three categories; namely, (1) reactive near-field; (2) radiated near-field and (3) radiated far-field. "Inductive" charging systems operate in the reactive near-field region. In inductive power systems, power is typically transferred over short distances by magnetic fields using inductive coupling between coils of wire, such as receiving coil 708 or by electric fields using capacitive coupling between electrodes. In radiative power systems (e.g. radiated near-field and radiated far-field), power is typically transmitted by beams of electromagnetic (EM) energy. Radiative power systems can often transport energy for longer distances, but the ability of a receiving antenna to capture sufficient energy can be challenging, particular for applications where the size of the receiving antenna is limited.

In some cases, a transmitter (such as transmitter 704 of FIG. 6) and IMD 702 may operate between 10 kHz and 100 MHz within the patient's body. When so provided, the system may operate in the reactive near-field (as an inductive charging system). In some cases, the transmitter 704 may transmit the near-field energy such that a receiving coil (i.e., receiving coil 708) may capture the near-field energy and provide it to the charging circuitry 710. In some cases, the charging circuitry 710 may be configured to convert the received near-field energy into a form that may be used to recharge the rechargeable power source 712. In some cases, the receiving coil 708 may be configured to receive sufficient near-field energy from a wavelength band of near-field energy transmitted from outside the patient 700 (FIG. 6) to recharge the rechargeable power source 712 at a rate faster than the rechargeable power source 712 is depleted by powering the IMD 702 when the wavelength band of near-field energy is transmitted at an intensity that does not cause heat damage to the patient 700. In various embodiments, the IMD 702 may include a temperature sensor (not shown) that may be configured to determine if self-heating of the IMD 702 is occurring when the rechargeable power source 712 is charging. In some cases, the housing 706 of the IMD 702 has a substantially cylindrical profile and the receiving coil 708 may be conformed to the substantially cylindrical profile of an inner and/or outer surface of the housing 706. In some cases, there may be two or more coils within or on the IMD 702. For example, two or more coils may be placed inside the housing 706. In some cases, there may be three coils oriented orthogonal to one another.

The rechargeable power source 712 may be any type of rechargeable battery, and may take a three dimensional shape that facilitates incorporation of the rechargeable battery into the device housing 706. In some cases, the rechargeable power source 712 may not be a battery at all, but instead may be a super capacitor, other charge storage device or combination of different types of energy storage devices. As will be appreciated, in some cases the device housing 706 may have a cylindrical or substantially cylindrical shape, in which case the rechargeable power source 712 having a cylindrical or annular profile, such as a button battery or an elongated (in height) battery having a substantially cylindrical shape, may be useful. It is recognized that there are possible tradeoffs in rechargeable battery shape and dimensions relative to performance, so these issues should be considered in designing the rechargeable power source 712 for a particular use. While FIG. 8 schematically shows a single rechargeable power source 712, in some cases there may be two, three or more distinct rechargeable power sources 712, each electrically coupled with the charging circuitry 710. For example, in some cases, there may be performance advantages in having multiple rechargeable power sources 712. In some instances, there may be packaging advantages to having multiple (and smaller) rechargeable power sources 712.

In some cases, the rechargeable power source 712 may be configured to power the IMD 702, including the therapeutic circuitry 714. In some instances, the therapeutic circuitry 714 and the rechargeable power source 712 may provide electrical signals to the electrodes 715, 719 and thus control the pacing/sensing electrodes 715, 719. In some instances, the therapeutic circuitry 714 may be configured to sense one or more signals via the electrodes 715, 719 and/or stimulate tissue via the electrodes 715, 719. As a result, the therapeutic circuitry 714 may pace, stimulate tissue, and/or sense a physiological condition at least partly in response to the one or more sensed signals. In some cases, the charging circuitry 710 and the therapeutic circuitry 714 may be located on distinct circuit boards or be manifested within distinct integrated circuits (ICs). In some cases, the charging circuitry 710 and the therapeutic circuitry 714, while shown as distinct elements, may be combined within a single IC or on a single circuit board.

While two electrodes 715, 719 are illustrated, it will be appreciated that in some instances the IMD 702 may include three, four or more distinct electrodes. Depending on the intended functionality of the IMD 702, as discussed above, the electrodes 715, 719 may be used for sensing and/or pacing the patient's heart. In some instances, for example, the IMD 702 may be a leadless cardiac pacemaker (LCP), an implantable monitoring device or an implantable sensor. In some cases, the electrodes 715, 719 may be used for communicating with other implanted devices and/or with external devices. In some cases, communication with other implanted devices may include conductive communication, but this is not required.

According to various embodiments, the controller 717 may be configured to monitor the operation of the IMD 702. For instance, the controller 717 may be configured to receive electrical signals from the charging circuitry 710. Based on the received signals, the controller 717 may detect the near-field energy received by the receiving coil 708 and generate a message regarding the near-field energy. For example, in some cases, the power transfer efficiency between the IMD 702 and a transmitter (e.g., transmitter 704) may depend on the relative orientation to one another and/or the distance between them. As such, when a transmit coil from the transmitter 704 is within a range of the receiving coil 708, a magnetic field may flow through the receiving coil 708 allowing the receiving coil 708 to receive the near-field energy. The charging circuitry 710 may use the near-field energy to charge the rechargeable power source 712 and send a signal to the controller 717 to indicate that the charging circuitry 710 is attempting to charge the rechargeable power source 712.

In some cases, the controller 717 may detect whether the signal meets a predetermined characteristic, condition or criteria. The predetermined characteristic, condition, or criteria may, for example, include a predetermined minimum energy capture rate by the receiving coil 708, a predetermined minimum voltage produced by the receiving coil 708, a predetermined minimum current produced by the receiving coil 708, and/or any other suitable characteristic or condition. In some situations, the rate at which the charging circuitry 710 is charging the rechargeable power source 712 may be less than the rate at which the rechargeable power source 712 is powering the IMD 702. As a result, the rechargeable power source 712 is still being depleted, albeit at a lower rate.

In some cases, the controller 717 may use the signal sent from the charging circuitry 710 (or other signal) to determine that the near-field energy from the transmitter and captured by the receiving coil 708 is not strong enough to meet the predetermined characteristic, condition or criteria. The controller 717 may then send a communication message (e.g., a signal) to the transmitter indicating that the rechargeable power source 712 is not charging sufficiently, and a user (e.g., the patient 700) may be presented with a notification. In some cases, the controller 717 may send a communication message to an external device, such as the patient's mobile phone or other device to alert the patient. In further embodiments, the message could be sent to a database over a network connection.

In some cases, the transmitter may include a user-interface with illuminating devises such as LED's, or audio devices, such as speakers or buzzers, to provide the notification. For example, a "not charging" message may be displayed using a red LED and a "charging" message may be displayed using a green LED. In this case, the patient 700 may observe that the red LED has turned on and may then realign the transmitter in response. In some cases, such a realignment may change the magnetic flux through the receiving coil 708 and increase the near-field energy received by the receiving coil 708. The charging circuitry 710 may then use the increased near-field energy to charge the rechargeable power source 712 and send a signal to the controller 717 to indicate that the charging circuitry 710 is once again, attempting to charge the rechargeable power source 712. In this case, the rate at which the charging circuitry 710 is charging the rechargeable power source 712 may be deemed acceptable. The controller 717 may then send a communication message to the transmitter indicating that the rechargeable power source 712 is charging. In this case, the "charging" message may be displayed to the patient by the green LED turning on.

As discussed above, in various embodiments, the controller 717 may be located on a pre-programmed VLSI chip, an ASIC, or on a programmable microprocessor. In some examples, regardless of whether the controller 717 is located on pre-programmed chip or a programmable microprocessor, the controller 717 may be programmed with logic where the controller 717 can send a message to alert the patient 700 about predetermined criteria or a high-priority condition requiring the patient's attention. For example, when the transmit coil from the transmitter 704 is within a range of the receiving coil 708, the magnetic field may flow through the receiving coil 708 allowing the receiving coil 708 to receive the near-field energy. The charging circuitry 710 may then use the near-field energy to charge the rechargeable power source 712. In this embodiment, the controller 717 may be programmed to detect whether the near-field energy received is great enough to charge the rechargeable power source 712. In another embodiment, the controller 717 may be programmed to detect whether the near-field energy received is great enough to charge the rechargeable power source 712 within a certain amount of time. For example, in some cases, the controller 717 may be programmed to detect whether the received near-field energy will fully charge the rechargeable power source 712 in 1 hour. In some cases, the controller 717 may be programmed to detect whether the received near-field energy will fully charge the rechargeable power source 712 in 8 hours. In some cases, the controller 717 may be programmed to detect whether the received near-field energy will fully charge the rechargeable power source 712 in 24 hours. In various embodiments, the charging of the rechargeable power source 712 or the rate at which the rechargeable power source 712 is charging may be predetermined characteristics, conditions or criteria, and the controller 717 may be programmed to alert the patient when there is a failure to charge the rechargeable power source 712 or a failure to meet the rate of charging or some other predetermined characteristic, condition or criteria.

Continuing with the current example, if the controller 717 detects that the rechargeable power source 712 is not charging or the rechargeable source 712 will not fully charge within a certain amount of time, the controller 717 may be programmed to send a communication message to the transmitter that turns on a red LED indicating that the rechargeable power source 712 is not charging adequately. Furthermore, if the controller 717 detects that the rechargeable power source 712 is charging or the rechargeable source 712 will fully charge within a certain amount of time, the controller 717 may be further programmed to send a communication message to the transmitter that turns on a green LED indicating that the rechargeable power source 712 is adequately charging. In some cases, the controller 717 may send a communication message to an external device, such as the patient's mobile phone. In some cases, when the transmitter receives a communication message that indicates the rechargeable power source 712 is not charging, the rechargeable source 712 will not fully charge within a certain amount of time, and/or the power received by the receiving coil 708 does not meet some other predetermined characteristic, condition or criteria, the transmitter may increase the transmit power to the transmit coil. This may include adjusting the frequency and/or amplitude of the signal provided to the transmit coil.

Figure 9:
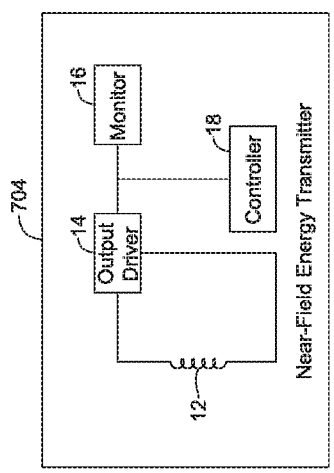
FIG. 9 is a schematic diagram of an illustrative transmitter according to an example of the disclosure.

FIG. 9 provides an illustrative but non-limiting example of at least some of the components within an illustrative near-field energy transmitter 704. As shown, the illustrative near-field energy transmitter 704 may include a transmit coil 12, an output driver 14, a monitor 16, and a controller 18. In certain cases, the transmit coil may be configured to transmit near-field energy to an IMD (e.g., IMD 702) through inductive coupling. As discussed above, inductive coupling is the near-field wireless transmission of electrical energy between the transmitter 704 and the IMD 702. In some cases, the transmitter 704 may transfer power from the transmit coil 12 to a device inductor (e.g., receiving coil 708) by a magnetic field. In some cases, a signal generator (not shown) may generate an AC through the transmit coil 12 and create an oscillating magnetic field. The magnetic field may pass through the receiving coil 708 and induce an alternating EMF, which creates an AC in the IMD 702 to power a load (e.g., rechargeable power source 712).

In some cases, the transmit coil 12 may be fitted with a ferrite core. The high permeability, relative to the surrounding environment, may cause the magnetic field to be concentrated in the ferrite core. In some cases, the use of the ferrite core can concentrate the strength and increase the effect of magnetic fields produced by electric currents through the transmit coil 12. The magnetic field may also be confined and guided, using the ferrite core, and may improve coupling, thus, improving the transfer of power.

In various embodiments, the output driver 14 may be configured to drive the transmit coil 12 at a given frequency and amplitude. In certain embodiments, the output driver 14 may adjust the frequency and/or amplitude at which the near-field energy is transmitted. In some cases, the near-field energy received may depend on the inductive coupling between the transmit coil 12 and the receiving coil 708 and in some instances, the inductive coupling may depend on the frequency at which the transmit coil 12 is driven. As such, the near-field energy, and thus the power, transmitted by the transmit coil 12 may be larger when the transmit coil 12 is driven by the output driver 14 at one frequency over another frequency. In some cases, the closer the frequency at which the transmit coil 12 is driven is to a resonant frequency, the greater the power that is transmitted between the transmitter 704 and the IMD 702. At the resonant frequency, the transmit coil 12 and the receiving coil 708 may achieve resonant inductive coupling, where the transmitted power may reach a maximum. In some instances, when the transmit coil 12 and the receiving coil 708 achieve resonant inductive coupling, the transmitter 704 and the IMD 702 may interact with each other more strongly than they do with non-resonant objects, and power losses due to absorption in stray nearby objects may be reduced.

In some cases, a monitor 16 may be configured to detect a measure of the transmitted power from the transmit coil 12. The transmitted power may be dependent on the impedance matching between the transmitter (including the transmit coil) and the receiver of the IMD 702. The impedance of the receiver of the IMD 702 may include the input impedance of the receiving coil 708, the input impedance of the charging circuitry 710, and the impedance of the medium between the transmit coil and the receiving coil 708 (e.g. the patient's body). Since the impedance of the patient's body may change over time (e.g. with respiration, posture, activity level, etc.), the transmitted power may vary over time. To help increase the transmitted power, the transmitter may adjust, sometimes actively adjust, the frequency of the transmitted field to better match the impedance of the receiver of the IMD 702 (sometimes including the impedance of the patient's body therebetween).

In some cases, a controller 18 of the transmitter 704 may be operatively coupled to output driver 14 and monitor 16. The controller 18 may be configured to cause the output driver 14 to adjust the transmit frequency of the near-field energy across two or more transmit frequencies, identify the transmit power of the near-field energy at each of the two or more transmit frequencies using the monitor 16, select the transmit frequency of the two or more transmit frequencies that results in a transmit power that has a predetermined characteristic, condition or criteria, and set the transmit frequency of the output driver 14 to the selected transmit frequency.

In one example, the transmit coil 12 and the receiving coil 708 may achieve resonant inductive coupling at a resonant frequency. The resonant frequency may depend on, for example, the impedances of the transmit coil 12, the impedance of the receiving coil 708 and the impedance of the patient's body therebetween. As discussed above, the power transmitted by the transmit coil 12 may be larger as the transmit frequency becomes closer to the resonant frequency. The monitor 16 may detect the power transmitted at two or more different transmit frequencies, and the controller 18 may use this information to identify a frequency that will deliver sufficient power to the IMD 702. In some cases, the controller 18 may attempt to identify the resonance frequency. In some cases, the controller 18 may identify a suitable frequency for each of several detectable conditions, such an inhalation phase of the patient, an exhalation phase of the patient, the posture of the patient, the activity level of the patient, and/or any other detectable condition. Then, when a particular condition is detected, the controller 18 may transmit power at the corresponding identified frequency.

In some cases, the controller 18 may periodically monitor the operation of the transmitter 704 such that the transmitter 704 continues to update the suitable frequencies. In some cases, the monitoring may be initiated according to a triggering condition. For example, the controller 18 may detect a decrease in the power transmitted to the IMD 702 when the transmitter 704 is being run at a driven frequency. The controller 18 may then instruct the output driver 14 to adjust the frequencies to one or more other frequencies and instruct the monitor 16 to detect the transmitted powers at each of these frequency. The controller 18 may then identify the transmitted power values for each of these frequencies and store the transmitted power values. The controller 18 may then compare the transmitted power values and determine the frequency that delivers the maximum transmitted power to the IMD 702. The controller 18 may then set the output driver 14 to drive the transmit coil 12 at this frequency.

As discussed herein, power transmission may reach a maximum when the transmit coil 12 and the receiving coil 708 achieve resonant inductive coupling. Resonant inductive coupling may occur when the transmit coil 12 and the receiving coil 708 are configured to resonant at the same frequency and the transmit frequency equals the resonant frequency. In some cases, to configure the transmit coil 12 and the receiving coil 708 to resonant at the same or similar frequency, the impedance of the transmitter 704 may be changed to conform with the impedance of the IMD 702 (and in some cases, the patient's body therebetween).

In some instances, the impedance of the IMD 702 (and in some cases, the patient's body therebetween) may vary over time. For example, during the lifespan of the IMD 702, the internal impedance may change due to the aging of the circuitry of an IMD 702. In another example, the impedance may be affected by an implantation location of the IMD 702, and as a result, minor shifts or changes from the implantation location and/or orientation may change the internal impedance of the IMD 702. In addition, the location of the transmitter 704 relative to the IMD 702 may affect the impedance between the transmitter 704 and the IMD 702 (sometimes including the impedance of the patient's body therebetween), which may also affect the resonant frequency and the transmission of power. Also, changes in body posture, activity level, respiration and other characteristics of the patient may affect the impedance between the transmitter 704 and the IMD 702. To help compensate for these changes, the impedance of the transmitter may be changed over time. More specifically, the impedance of the output driver 14 and the transmit coil 12 may be adjusted to match the impedance of the IMD 702 (702 (sometimes including the impedance of the patient's body therebetween). This may help bring their resonance frequencies into alignment. Therefore, in some cases, the controller 18 may be configured to instruct the output driver 14 to adjust the impedance of the transmitter 704 such that the impedance of the output driver 14 and the transmit coil 12 may conform with the impedance of the IMD 702 and the impedance of the environment separating the transmitter 704 and the IMD 702 (e.g. the patient's body).

In some cases, the controller 18 may periodically monitor the operation of the transmitter 704 such that the transmitter 704 continues to transmit acceptable power. In some cases, the monitoring may be initiated according to a triggering condition. For example, the monitor 16 may detect a decrease in the power transmitted to the IMD 702. The controller 18 may then instruct the output driver 14 to adjust the impedance to change the resonance frequency of the transmitter 704 and drive the transmit coil 12 at the adjusted resonant frequency. The controller 18 may then instruct the monitor 16 to detect the transmitted power. This may be repeated from time to time.

In some cases, near-field energy transmitter 704 is operating to recharge a single IMD in which case output driver 14 and controller 18 are configured to optimally recharge the single IMD and monitor 16 indicates the status of the recharge of the single IMD. In other cases, the system may contain 2 or more IMDs, as indicated in FIG. 3, and near-field energy transmitter 704 operates to recharge the multiple IMDs. In this case, output driver 14 and controller 18 may be configured to optimally recharge the multiple IMDs and monitor 16 may indicate the status of the recharge of the multiple IMDs. In a system with multiple rechargeable IMDs, the transmitter 704 may simultaneously recharge both IMDs or preferentially recharge one or more IMDs based on the charge status of all the IMDs.

Figure 10:
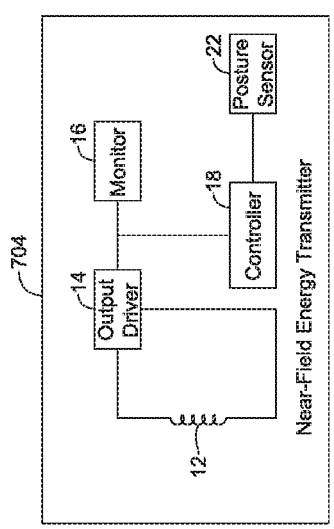
FIG. 10 is a schematic diagram of another illustrative transmitter according to an example of the disclosure.

FIG. 10 provides another illustrative but non-limiting example of at least some of the components within the near-field energy transmitter 704. The configuration and operation of the near-field energy transmitter 704 and its elements may be similar to the configuration and operation of the near-field energy transmitter 704 and its elements described with respect to FIG. 9. In some cases, as seen in FIG. 10, the near-field energy transmitter 704 may also include a posture sensor 22. As discussed herein, in some cases, the location of the transmitter 704 relative to the IMD 702 may affect the impedance between the transmitter 704 and the IMD 702 which may also affect the transmission of power. Furthermore, the relative location of the IMD 702 within the patient 700 may depend on a posture of the patient 700. In some cases, the posture sensor 22 may be configured to detect the posture of the patient 700 and the controller 18 may be configured use the detection of the posture and respond to changes in the posture of the patient 700 to control the operation of the transmitter 704. For example, when the transmitter 704 is placed in the range to charge the IMD 702, the controller 18 may instruct the posture sensor 22 to detect the posture of the patient 700, which may be a first position. The controller 18 may then control the operation of the transmitter 704 to determine, select, and set the transmit frequency at which the output driver 14 drives the transmit coil 12 to achieve an acceptable power transmission to the IMD 701. The controller 18 may then associate this transmit frequency with the first position.

In some cases, the controller 18 may detect a decrease in the power transmitted to the IMD 702. In response, the controller 18 may instruct the posture sensor 22 to detect the posture of the patient 700, which may now be a second position different from the first position. The controller 18 may then control the operation of the transmitter 704 to determine, select, and set the transmit frequency at which the output driver 14 drives the transmit coil 12 to achieve an acceptable power transmission to the IMD 701. The controller 18 may then associate this transmit frequency with the second position.

In some cases, the controller 18 may once again detect a decrease in the power transmitted to the IMD 702. In response, the controller 18 may instruct the posture sensor 22 to detect the posture of the patient 700, which may now be a third position that is different from the first position and the second position. The controller 18 may then control the operation of the transmitter 704 to determine, select, and set the transmit frequency at which the output driver 14 drives the transmit coil 12 to achieve an acceptable power transmission to the IMD 701. The controller 18 may then associate this transmit frequency with the third position.

In some cases, at a later time, the controller 18 may monitor the posture of the patient via the posture sensor 22. When the posture of the patient 700 is detected to be the first position, the controller 18 may automatically switch to the transmit frequency that is associated with the first position. When the posture of the patient 700 is detected to be the second position, the controller 18 may automatically switch to the transmit frequency that is associated with the second position. When the posture of the patient 700 is detected to be the third position, the controller 18 may automatically switch to the transmit frequency that is associated with the third position.

A similar approach may be used in conjunction with a respiration sensor, an activity level sensor and/or any other suitable sensor. For example, with respect to a respiration sensor, the controller 18 may associate a first transmit frequency with an inhalation phase of the respiration cycle and a second transmit frequency with an exhalation phase of the respiration cycle. Then, when the respiration sensor detects an inhalation phase of the respiration cycle, the controller 18 may automatically switch to the first transmit frequency, and when the respiration sensor detects an exhalation phase of the respiration cycle, the controller 18 may automatically switch to the second transmit frequency.

Figure 11:
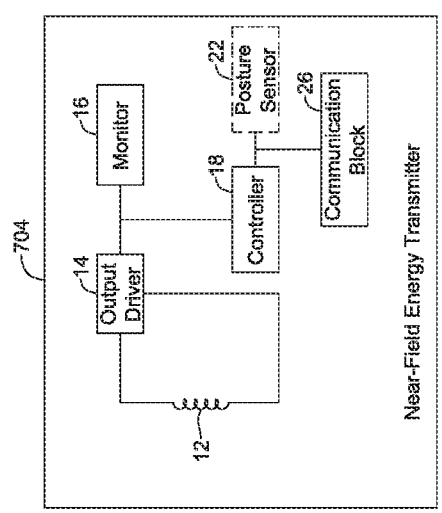
FIG. 11 is a schematic diagram of another illustrative transmitter according to an example of the disclosure.

FIG. 11 provides another illustrative but non-limiting example of at least some of the components within the near-field energy transmitter 704. The configuration and operation of the transmitter 704 and its elements may be similar to the configuration and operation of the transmitter 704 and its elements described with respect to FIG. 9. Furthermore, in some instances, the transmitter 704 may include the posture sensor 22 similar to the posture sensor 22 described with respect to FIG. 10. In some cases, as seen in FIG. 11, the transmitter 704 may include a communication block 26. The communication block 26 may be configured to communicate with devices such as sensors, other medical devices such as the IMD 702, and/or the like, that are located externally to the transmitter 704. Such devices may be located either external or internal to the patient's 700 body. Irrespective of the location, external devices (i.e. external to the transmitter 704 but not necessarily external to the patient's 700 body) can communicate with the transmitter 704 via communication block 26 to accomplish one or more desired functions. The communication block 26 may be configured to use one or more methods for communicating with the IMD 702. For example, the communication block 26 may communicate via radiofrequency (RF) signals, inductive coupling, optical signals, acoustic signals, conducted communication signals, and/or any other signals suitable for communication. In some cases, the transmitter 704 may communicate information, such as sensed electrical signals, data, instructions, messages, R-wave detection markers, etc., to the IMD 702 through the communication block 26. The transmitter 702 may additionally receive information such as signals, data, instructions and/or messages from the IMD 702 through the communication block 26, and the transmitter 704 may use the received signals, data, instructions and/or messages to perform various functions, such as charging the rechargeable power source 712, storing received data, and/or performing any other suitable function. In some cases, the communication block 26 may be used to enable communication between the transmitter 704 and the IMD 702 using the near-field energy. Near-Field communication is a wireless form of short range communication using near field magnetic flux for data transmission.

In certain instances, the communication block 26 may receive messages or information from the IMD 702 regarding the power transmitted from the near-field energy produced by the transmit coil 12. For example, when the patient 700 wants to charge the IMD 702, they may bring the transmitter 704 close to where the IMD 702 is located. In some cases, the communication block 26 may look for or poll for the nearby IMD 702 using the near-field energy. The IMD 702 may listen and respond by sending a signal back to the communication block 26 when the transmitter 704 is close enough. The communication block 26 may then decipher the signal and may send a signal to the controller 18 that the IMD 702 is within range and the controller 18 may begin the charging process. The controller 18 may then attempt to charge the rechargeable power source 712 by instructing the output driver 14 to drive the transmit coil 12 such that the near-field energy is transmitted at a first transmit frequency and/or amplitude. The communication block 26 may then receive a message from the IMD 702 regarding whether the transmitted power meets predetermined characteristic, condition or criteria. The communication block 26 may then send the message to the controller 18. In some instances, the controller 18 may perform a function or functions based on whether the transmitted power meets the predetermined characteristic, condition or criteria. For example, the strength of the transmitted power to the IMD 702 may not be enough to charge the rechargeable power source 712. As a result, the IMD 702 may send a message to the communication block 26 indicating that the transmitted power does not meet predetermined "charging" criteria. The communication block 26 of the transmitter 704 may then send the signal to the controller 18. Additionally or alternatively, in some cases, the communication block 26 may send a communication message to an external device, such as the patient's mobile phone. The controller 18 may then, for example, illuminate a red LED on a user-interface of the transmitter 704 to inform the patient 700 that the IMD 702 is not charging properly. In some cases, the patient may adjust the position of the transmitter 704 in an attempt to better align the transmitter 704 with the IMD 702. Alternatively, or in addition, the controller 18 may adjust the transmit frequency and/or transmit amplitude of the output driver 14 and thus the transmit coil 12 in an attempt to increase the transmitted power to the IMD 702. If the transmitted power is deemed sufficient, the IMD 702 may send a signal to the communication block 26 of the transmitter 704 indicating that the transmitted power meets the "charging" criteria. The communication block 26 may then send the signal to the controller 18. Additionally or alternatively, in some cases, the communication block 26 may send a communication message to the patient's mobile phone. In some cases, the controller may illuminate a green LED on the user-interface of the transmitter 704 to inform the patient 700 that the IMD 702 is now properly charging.

Figure 12:
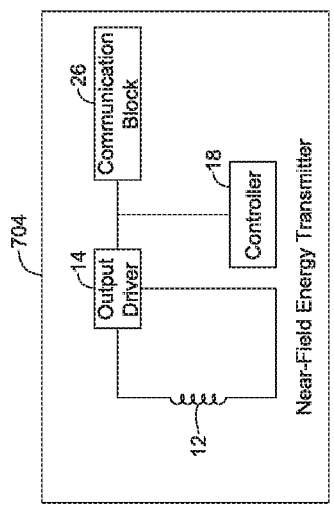
FIG. 12 is a schematic diagram of another illustrative transmitter according to an example of the disclosure.

FIG. 12 provides another illustrative but non-limiting example of at least some of the components within the near-field energy transmitter 704. The configuration and operation of the transmitter 704 and its elements may be similar to the configuration and operation of the transmitter 704 and its elements described with respect to FIG. 9 and the transmitter 704 and its elements described with respect to FIG. 11. For example, when the patient 700 wants to charge the IMD 702, they may bring the transmitter 704 close to where the IMD 702 is located. In some cases, the communication block 26 may look for or poll for the nearby IMD 702 using the near-field energy. The IMD 702 may listen and respond by sending a signal back to the communication block 26 when the transmitter 704 is close enough. The communication block 26 may then decipher the signal and may send a signal to the controller 18 of the transmitter 704 that the IMD 702 is within range and the controller 18 may begin the charging process.

In some cases, the controller 18 may attempt to charge the rechargeable power source 712 by instructing the output driver 14 to drive the transmit coil 12 such that the near-field energy is transmitted at a transmit frequency and at a transmit amplitude. The communication block 26 may receive a message from the IMD 702 regarding whether the transmitted power meets one or more predetermined characteristics, conditions or criteria. The communication block 26 may forward the message to the controller 18. In some instances, the controller 18 may perform a function or functions based on whether the transmitted power meets the one or more predetermined characteristics, conditions or criteria.

In one example, the patient 700 may want to charge the IMD 702 within 1 hour. In such a case, a predetermined criteria may be whether the rate at which the rechargeable power source 712 is charging is great enough to fully charge the rechargeable power source 712 within 1 hour. In some cases, this rate may the rate needed to charge the rechargeable power source 712 from a completely discharged state to a fully charged state, or it may be the rate needed to charge the rechargeable power source 712 from the currently charged state (e.g. half charged) to a fully charged state (e.g. from half charged to fully charged). If the transmitted power to the IMD 702 is not sufficient to charge the rechargeable power source 712, the IMD 702 may send a message to the communication block 26 of the transmitter 704 indicating that the transmitted power (power received at the IMD 702) does not meet a "charging" criteria. The communication block 26 may forward the message to the controller 18. The controller 18 may illuminate a red LED on a user-interface of the transmitter 704 to inform the patient 700 that the IMD 702 is not charging. In some cases, the patient may adjust the position of the transmitter 704 in an attempt to better align the transmitter 704 with the IMD 702. Alternatively, or in addition, the controller 18 may adjust the transmit frequency and/or transmit amplitude, and instruct the output driver 14 to drive the transmit coil 12 at the adjusted transmit frequency and/or transmit amplitude. This time, the transmitted power to the IMD 702 may be sufficient to charge the rechargeable power source 712 but not within one hour. As a result, the IMD 702 may send a message to the communication block 26 indicating that the transmitted power still does not meet the "rate of charging" criteria. The communication block 26 may then send the message to the controller 18. In some cases, the controller 18 may illuminate a yellow LED on the user-interface of the transmitter 704 to show that the IMD 702 is charging, but not fast enough to be fully charged within 1 hour. In some cases, the patient may again adjust the position of the transmitter 704 in an attempt to better align the transmitter 704 with the IMD 702. Alternatively, or in addition, the controller 18 may adjust the transmit frequency and/or transmit amplitude, and instruct the output driver 14 to drive the transmit coil 12 at the adjusted transmit frequency and/or transmit amplitude. This time, the transmitted power to the IMD 702 may be sufficient to charge the rechargeable power source 712 within one hour. As a result, the IMD 702 may send a message to the communication block 26 indicating that the transmitted power meets the "rate of charging" criteria. The communication block 26 may then forward the message to the controller 18. In some cases, the controller 18 may illuminate a green LED on the user-interface of the transmitter 704 to show that the IMD 702 is charging at a rate that is fast enough to fully charge the rechargeable power source 712 within 1 hour. This is just one example.

Figure 13A:
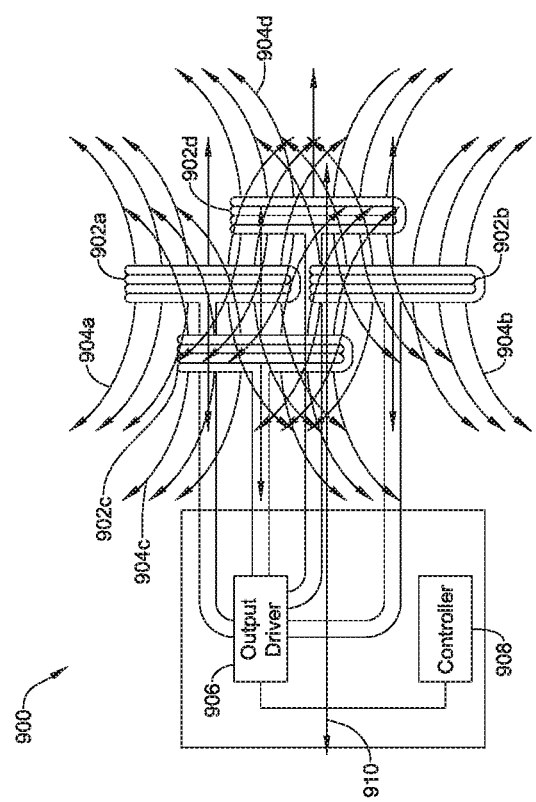
FIG. 13A provides a side-view of an illustration of a coil configuration for a near-field transmitter containing multiple transmit coils.
Figure 13B:
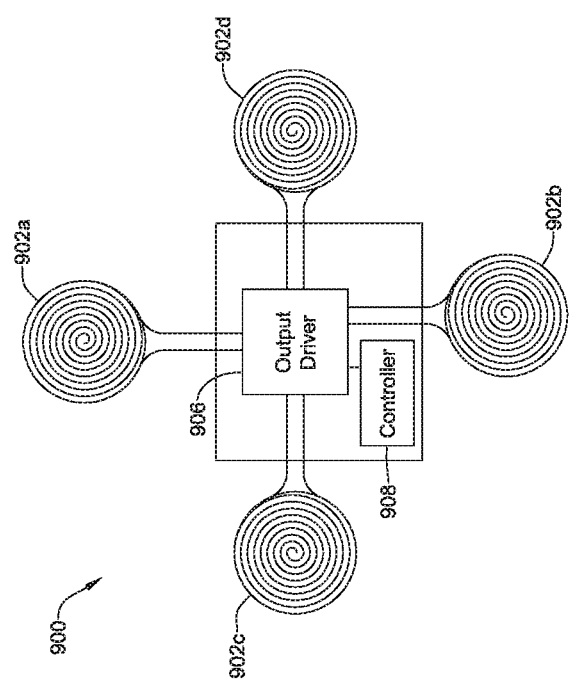
FIG. 13B provides a front-view of the illustration of the coil configuration for a near-field transmitter containing multiple transmit coils.

FIG. 13A provides a schematic side-view and FIG. 13B provides a front-plan view of an illustration of a coil configuration 900 for a near-field transmitter (such as transmitter 704 of FIG. 9) containing multiple transmit coils 902a-902d. Each of the coils 902a-902d can be independently driven by output driver 906 to create near-field magnetic fields 904a-904d. Magnetic fields 904a-904d form composite magnetic field 910. Controller 908 may adjust the currents in coils 902a-902d thereby shifting the spatial peak (i.e. the transmit vector) of the composite magnetic field 910 to increase the power delivered to IMD 702. Adjusting the spatial peak of the composite magnetic field 910 may increase the power delivered to IMD 702 without the need for the patient to move transmitter 704.

Figure 14A:
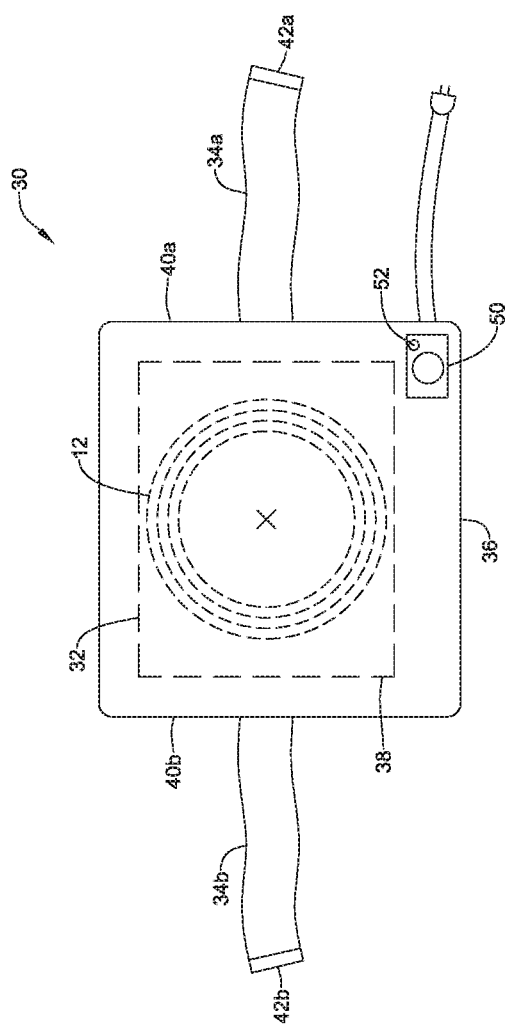
FIG. 14A is an illustrative flexible substrate that may house a transmit coil according to an example of the disclosure.

FIG. 14A provides an illustrative but non-limiting example of a flexible substrate 30 that may house the transmit coil 12. The configuration and operation of the transmit coil 12 may be similar to the configuration and operation of the transmit coil 12 described with respect to FIGS. 9-12 when used in conjunction with the other elements included in the transmitter 704 described with respect to FIGS. 9-12.

In some cases, the substrate 30 may be formed of a flat woven fabric that defines a pocket 38. In some embodiments, the pocket 38 may include a flexible flap-like closure (not shown) which may be folded over the pocket 38 to contain the transmit coil 12 therein. According to various embodiments, the transmit coil 12 may be configured with low-resistive windings and an air-core front end. Furthermore, in some cases, the transmit coil 12 may be composed of a Litz wire and the spacing of the windings of the transmit coil 12 may be determined to potentially manage the thermal heating relating to the transmit coil 12.

In certain embodiments, the substrate 30 may be composed of one or more types of material that is commercially available and characterized by its flexibility and its ability to fit snuggly and/or comfortably to a piece of furniture (e.g., chair 48, from FIG. 14B) or a patient (e.g., patient 700, from FIG. 14C). Additionally, and in some cases, the substrate 30 may include target fiducials 32 sewn, printed, or painted on the surface of the substrate 30. In various embodiments, the target fiducials 32 may be used by the patient to assist the patient in aligning the transmit coil 12 with an IMD (e.g., IMD 702) within a patient (e.g., patient 700, from FIG. 14C).

In some cases, the substrate 30 may also be provided with supports for supporting the pocket 38 at various positions on the patient 700 (from FIG. 14C) or on a piece of furniture, such as the chair 48 (from FIG. 14B), a bed, a couch, etc. By way of example, the substrate 30 may include opposed elongated flexible fabric strap members 34a, 34b which are secured to the substrate 30 and extend normal to the opposed side edges 40a, 40b, respectively. The straps 34a, 34b may be formed of a suitable woven polyester fabric, for example. The distal ends of the straps 34a, 34b may be attached to connector members 42a, 42b that may take many forms, such as hooks, Velcro, screws, pins, clasps, buckles or another type of fastener that may secure connector members 42a, 42b to one another, respectively, after the position of the straps 34a, 34b are adjusted to properly secure the substrate 30 in a preferred position on the back of the chair 48, as shown in FIG. 14B, or on the patient's body 700, as shown in FIG. 14C.

In various embodiments, the substrate 30 may include a ferromagnetic shield (not shown). In certain configurations, the ferromagnetic shield may be located on a side of the transmit coil 12 that is opposite or faces away from the IMD 702. Such a ferromagnetic shield may help direct or focus the electromagnetic energy toward the IMD 702.

In some instances, the effectiveness of the ferromagnetic shield may depend on the material used, its thickness, the size of the shielded volume and the frequency of the fields of interest and the size, shape and orientation of apertures in a shield to an incident electromagnetic field. In some cases, the material used may include sheet metal, a metal screen, or metal foam. In some cases, the substrate 30 may be coated with metallic ink or similar material. The ink may include a carrier material loaded with a suitable metal, typically copper or nickel, in the form of very small particulates. It may be sprayed on the pocket 38 and, once dry, may produce a continuous conductive layer of metal. These are just examples.

In some cases, the ferromagnetic shield may be made of high magnetic permeability metal alloys, such as sheets of Permalloy and Mu-Metal, or with nanocrystalline grain structure ferromagnetic metal coatings. These materials may draw a stray magnetic field into themselves and provide a path for the magnetic field around the shielded volume. The effectiveness of this type of shielding may depend on the shield's permeability, which may drop off at low magnetic field strengths and at high field strengths where the shield becomes saturated. As a result, to achieve low residual fields, the ferromagnetic shield may include several enclosures, one inside the other, each of which successively may reduce the stray fields.

In various cases, active shielding may be used by creating a field with electromagnets to cancel the ambient field within the volume outside of the body. Solenoids and Helmholtz coils are types of coils that can be used for this purpose. Additionally, superconducting materials can expel magnetic fields via the Meissner effect.

In some cases, the flexible substrate 30 may include a user-interface 50 with illuminating devises such as LED's 52, or audio devices, such as speakers 54, to display or issue a human perceptible alert if the transmit coil 12 is deemed to be misaligned with the IMD 702. For example, in some cases, misalignment of the transmit coil 12 with the IMD 702 may cause the IMD 702 to not charge sufficiently when the near-field energy is applied and charging is expected. As a result, the LED 52 may be illuminated and/or the speakers 54 may release a "buzz" sound. The patient 700 may observe the illumination of the LED 52 and/or hear the "buzz" from the speakers 54 and realign the transmit coil 12 until the LED 52 is no longer illuminated and/or the speakers 54 stop releasing the "buzz" sound.

Referring now to FIG. 14B, the substrate 30 may also be configured as an elongated pad or pillow-like member with the transmit coil 12 disposed in the pocket 38 in the manner described above. In certain embodiments, there may be several transmit coils disposed in the pocket 38 to potentially increase the power transmission and decrease the charging time of the IMD 702. In some cases, a transmit coil may be selected from the transmit coils that offers the most efficient power transmission and potentially, the least amount of charging time for the IMD 702. Since the substrate 30 may be substantially flexible, the substrate 30 may be attached to a chair 48 and used as a lumbar pillow or as a neck or shoulder support while the transmit coil 12 applies the near-field energy, for example. In some cases, the substrate 30 may be attached to the chair 48 by wrapping the straps 34a, 34b around the chair 48 and attaching the connector members 42a, 42b to one another. Furthermore, to assist in aligning the transmit coil 12 with the IMD 702, target fiducials 32 may be used to show the patient where the patient 700 should position their torso relative to the transmit coil 12. As a result, the inductive coupling between the transmit coil 12 and a receiving coil of the IMD 702 may be enhanced and help increase the power transmission of the near-field energy.

Referring now to FIG. 14C, there is illustrated an illustrative position in which the substrate 30 may be worn by the patient 700. In some cases, because of the flexibility, the substrate 30 may conform to the contour of the body of the patient 700 to minimize discomfort and help the patient 700 don conventional outer garments which may not interfere with the substrate 30 or vice versa. In certain embodiments, a garment worn by the patient 700 may be the flexible substrate 30, and the transmit coil 12 may be located in or on the garment (e.g., in the pocket of a shirt). In some cases, the substrate 30 may be attached to the patient 700 by wrapping the straps 34a, 34b around the torso of the patient 700 and attaching the connector members 42a, 42b to one another. Furthermore, to assist in aligning the transmit coil 12 with the IMD 702, target fiducials 32 may be used to show the patient where the patient 700 should position the pocket 38 relative to a body part (e.g., the chest). As a result, the inductive coupling between the transmit coil 12 and the receiving coil of the IMD 702 may be enhanced and help increase the power transmission of the near-field energy.

Figure 15A:
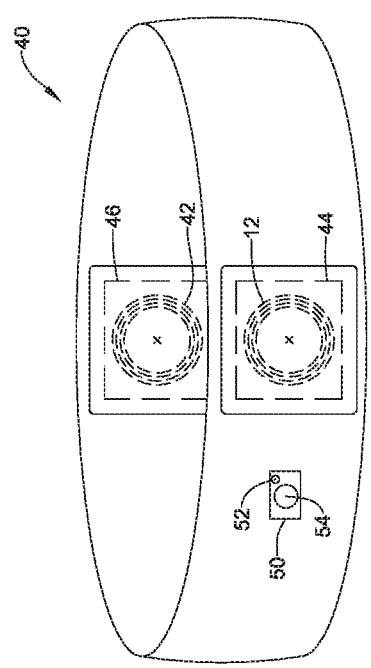
FIG. 15A is another illustrative flexible substrate that may house two transmit coils according to an example of the disclosure.

FIG. 15A provides an illustrative but non-limiting example of another flexible substrate 40 that may house the transmit coil 12 and another transmit coil 42. The configuration and operation of the transmit coils 12, 42 may be similar to the configuration and operation of the transmit coil 12 described with respect to FIGS. 14A-14C. Furthermore, the operation and configuration of the flexible substrate 40 may be similar to the flexible substrate 30 as described with respect to FIGS. 14A-14C. In some cases, the user-interface 50 may be used to display or issue a human perceptible alert if the transmit coil 12 and/or the transmit coil 42 are deemed to be misaligned with the IMD 702.

Referring now to FIG. 15B, there is illustrated one position in which the substrate 40 of FIG. 15A may be worn by the patient 700. In some cases, because of the flexibility, the substrate 40 may wrap around the patient's 700 torso and conform to the contour of the body of the patient 700 to minimize discomfort and enable the patient 700 to don conventional outer garments which may not interfere with the substrate 40 or vice versa. In certain embodiments, the transmit coil 12 may be configured to be located on a front part 56 of the patient 700 and the transmit coil 42 may be configured to be located on a back part 58 of the patient 700. However, in other embodiments, one or more of the transmit coils 12, 42 may be configured to be located on another part of the patient 700, such as a side part 60. In some cases, the positioning of the transmit coil 12 relative to the transmit coil 42 may provide an increase in the focusing, steering, guiding, shaping, or confining of the near-field energy toward the IMD 702. In some cases, the transmit coil 42 may be used as an electromagnetic shield for the transmit coil 12 by creating a field to cancel, absorb, or minimize the ambient or stray fields or eddy-currents. In various embodiments, the transmit coil 12 and transmit coil 42 may communicate with one another, by way of feedback for example, to determine the alignment between the transmit coil 12 and the transmit 42. In addition, in some cases, the user-interface 50 may be configured to receive the feedback and use the LED 52 and/or speakers 54 to display or issue a human perceptible alert if the transmit coil 12 is deemed to be misaligned with the transmit coil 42.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A near-field energy transmitter for charging an implantable medical device (IMD), the transmitter comprising:
   a transmit coil configured to transmit near-field energy to the IMD;
   an output driver for driving the transmit coil so that the transmit coil transmits the near-field energy at a transmit frequency, wherein the transmit frequency is adjustable;
   a monitor operatively coupled to the output driver for detecting a transmit power of the transmitted near-field energy;
   a controller operatively coupled to the output driver and the monitor, the controller configured to:
      cause the output driver to adjust the transmit frequency of the near-field energy across two or more transmit frequencies;
      identify the transmit power of the near-field energy at each of the two or more transmit frequencies using the monitor;
      select the transmit frequency of the two or more transmit frequencies that results in a transmit power that has a predetermined characteristic, wherein the predetermined characteristic is that the transmit power is the maximum transmit power identified for the two or more transmit frequencies; and
      set the transmit frequency of the output driver to the selected transmit frequency.

2. The near-field energy transmitter of claim 1, wherein at least one of the transmit frequencies is a resonant frequency of the output driver and transmit coil, and the output driver comprises an adjustable impedance that is adjustable to produce the resonance frequency.

3. The near-field energy transmitter of claim 1, wherein the controller is configured to detect a decrease in the transmit power at the selected transmit frequency, and in response:
   cause the output driver to adjust the transmit frequency of the near-field energy across two or more transmit frequencies;
   identify the transmit power of the near-field energy at each of the two or more transmit frequencies;

select the transmit frequency of the two or more transmit frequencies that results in a transmit power that has a predetermined characteristic; and set the transmit frequency of the output driver to the selected transmit frequency.

4. The near-field energy transmitter of claim 1, wherein the controller is configured to repeat from time to time the following:

cause the output driver to adjust the transmit frequency of the near-field energy across two or more transmit frequencies;

identify the transmit power of the near-field energy at each of the two or more transmit frequencies;

select the transmit frequency of the two or more transmit frequencies that results in a transmit power that has a predetermined characteristic; and set the transmit frequency of the output driver to the selected transmit frequency.

5. The near-field energy transmitter of claim 1, further comprising a posture sensor for detecting a posture of a patient in which the IMD is implanted, and wherein the controller is configured to identify a transmit frequency for each of two or more postures by:

using the posture sensor to detect when the patient is in one of the two or more postures, and when in the detected posture:

cause the output driver to adjust the transmit frequency of the near-field energy across two or more transmit frequencies;

identify the transmit power of the near-field energy at each of the two or more transmit frequencies using the monitor;

select the transmit frequency of the two or more transmit frequencies that results in a transmit power that has a predetermined characteristic; and associate the detected posture with the selected transmit frequency.

6. The near-field energy transmitter of claim 5, wherein the controller is further configured to subsequently detect when the patient is in one of the two or more postures, and in response, set the transmit frequency of the output driver to the transmit frequency that is associated with the detected posture.

7. The near-field energy transmitter of claim 1, further comprising a communication block for communicating with the IMD, and wherein the communication block is configured to receive one or more messages from the IMD regarding the transmit power that is received by the IMD.

8. The near-field energy transmitter of claim 7, wherein:

the output driver is configured to drive the transmit coil so that the transmit coil transmits the near-field energy at a transmit amplitude, wherein the transmit amplitude is adjustable; and the controller is configured to adjust the transmit amplitude of the near-field energy so that the transmit power that is received by the IMD meets a predetermined criteria.

9. The near-field energy transmitter of claim 8, wherein the one or more messages received from the IMD indicate whether the transmit power that is received by the IMD meets the predetermined criteria.

10. The near-field energy transmitter of claim 8, wherein the one or more messages received from the IMD indicate whether the transmit power that is received by the IMD does not meet the predetermined criteria.

11. The near-field energy transmitter of claim 1, further comprising a flexible substrate configured to conform to a patient and house the transmitter coil.

12. The near-field energy transmitter of claim 11, wherein the flexible substrate comprises a strap for securing the flexible substrate in place, and wherein the flexible substrate has target fiducials to indicate a torso position of the patient relative to the transmit coil.

13. The near-field energy transmitter of claim 11, further comprising a ferromagnetic shield along a side of the transmit coil that faces away from the IMD during use.

14. The near-field energy transmitter of claim 11, wherein the flexible substrate is configured to be worn by the patient.

15. The near-field energy transmitter of claim 14, further comprising a second transmit coil housed by the flexible substrate, wherein the transmit coil is configured to be located on a front of the patient and the second transmit coil is configured to be located on a side or back of the patient.

16. The near-field energy transmitter of claim 11, wherein the controller is further configured to issue a human perceptible alert if the transmit coil is deemed to be misaligned with the 1 MB.

17. A near-field energy transmitter for charging an implantable medical device (1 MB), the transmitter comprising:

a transmit coil configured to transmit near-field energy to the IMD;

an output driver for driving the transmit coil so that the transmit coil transmits the near-field energy at a transmit frequency and a transmit amplitude, wherein at least one of the transmit frequency and transmit amplitude is adjustable;

a communication block for communicating with the IMD, wherein the communication block is configured to receive one or more messages from the IMD regarding the transmit power that is received by the IMD; and a controller operatively coupled to the output driver and the communication block, the controller configured to adjust one or more of the transmit frequency and transmit amplitude of the near-field energy so that the transmit power that is received by the IMD meets a predetermined criteria.

18. The near-field energy transmitter of claim 17, wherein the one or more messages received from the IMD indicate:

whether the transmit power that is received by the IMD meets the predetermined criteria; and/or whether the transmit power that is received by the IMD does not meet the predetermined criteria.

19. A near-field energy transmitter for charging an implantable medical device (IMD), the transmitter comprising:

a transmit coil configured to transmit near-field energy to the IMD;

an output driver for driving the transmit coil so that the transmit coil transmits the near-field energy at a transmit frequency, wherein the transmit frequency is adjustable;

a monitor operatively coupled to the output driver for detecting a transmit power of the transmitted near-field energy;

a controller operatively coupled to the output driver and the monitor, the controller configured to:

cause the output driver to adjust the transmit frequency of the near-field energy across two or more transmit frequencies;

identify the transmit power of the near-field energy at each of the two or more transmit frequencies using the monitor;

select the transmit frequency of the two or more transmit frequencies that results in a transmit power that has a predetermined characteristic; and set the transmit frequency of the output driver to the selected transmit frequency;

wherein the controller is configured to detect a decrease in the transmit power at the selected transmit frequency, and in response:

cause the output driver to adjust the transmit frequency of the near-field energy across two or more transmit frequencies;

identify the transmit power of the near-field energy at each of the two or more transmit frequencies;

select the transmit frequency of the two or more transmit frequencies that results in a transmit power that has a predetermined characteristic; and set the transmit frequency of the output driver to the selected transmit frequency.

\* \* \* \* \*